United States Patent
Sharma et al.

(10) Patent No.: US 10,092,747 B2
(45) Date of Patent: Oct. 9, 2018

(54) MRI COMPATIBLE MEDICAL DEVICES

(71) Applicant: Nevro Corporation, Redwood City, CA (US)

(72) Inventors: Vivek Sharma, San Ramon, CA (US); Andre Walker, Monte Sereno, CA (US); Apratim Dixit, Menlo Park, CA (US)

(73) Assignee: NEVRO CORPORATION, Redwood City, CA (US)

( * ) Notice: Subject to any disclaimer, the term of this patent is extended or adjusted under 35 U.S.C. 154(b) by 411 days.

(21) Appl. No.: 14/702,377

(22) Filed: May 1, 2015

(65) Prior Publication Data

US 2015/0314123 A1    Nov. 5, 2015

Related U.S. Application Data

(60) Provisional application No. 61/987,891, filed on May 2, 2014.

(51) Int. Cl.
*A61N 1/08* (2006.01)
*A61N 1/05* (2006.01)

(52) U.S. Cl.
CPC ............... *A61N 1/08* (2013.01); *A61N 1/05* (2013.01); *A61N 1/0551* (2013.01); *A61N 1/086* (2017.08); *A61N 2001/086* (2013.01)

(58) Field of Classification Search
CPC .......... A61N 1/05; A61N 1/0551; A61N 1/08; A61N 1/086; A61N 2001/086
See application file for complete search history.

(56) References Cited

U.S. PATENT DOCUMENTS

| | | | |
|---|---|---|---|
| 7,174,720 B2 | 2/2007 | Chitre et al. | |
| 8,442,657 B2* | 5/2013 | Foster | A61N 1/056 607/122 |
| 2004/0743210 | 12/2004 | Morgan et al. | |
| 2005/0070972 A1* | 3/2005 | Wahlstrand | A61N 1/05 607/48 |
| 2005/0222658 A1 | 10/2005 | Hoegh et al. | |
| 2006/0200218 A1 | 9/2006 | Wahlstrand | |
| 2009/0099635 A1 | 4/2009 | Foster | |
| 2009/0270956 A1 | 10/2009 | Vase et al. | |
| 2011/0071593 A1 | 3/2011 | Parker et al. | |
| 2014/0058482 A1* | 2/2014 | Gupta | A61N 1/36142 607/63 |
| 2015/0272654 A1* | 10/2015 | Esch | A61B 18/082 606/34 |

OTHER PUBLICATIONS

International Application No. PCT/US/2015/028928, International Filing Date May 1, 2015, International Search Report and Written Opinion, dated Jul. 9, 2015, 9 pages.

* cited by examiner

*Primary Examiner* — Amanda Hulbert
(74) *Attorney, Agent, or Firm* — Sterne, Kessler, Goldstein & Fox P.L.L.C.

(57) ABSTRACT

A medical device for conducting electrical signal comprises an elongate member and a plurality of cables. Each cable may have three concentric layers: a first layer with an inner conductor, a second layer with an inner insulator, and a third layer with an outer conductor. The inner insulator electrically isolates the outer conductor from the inner conductor.

56 Claims, 25 Drawing Sheets

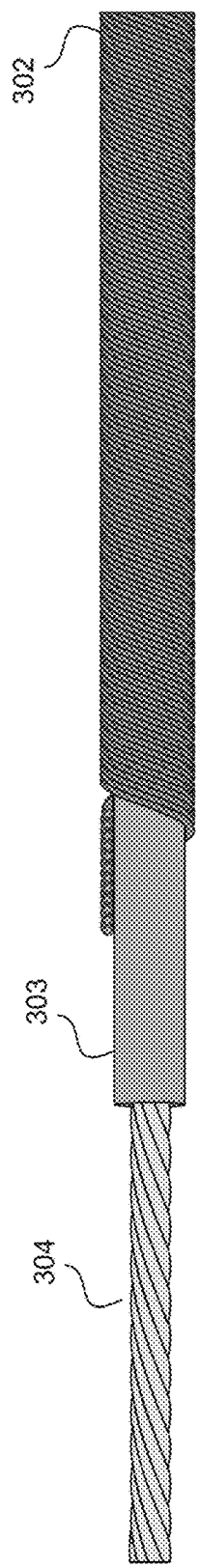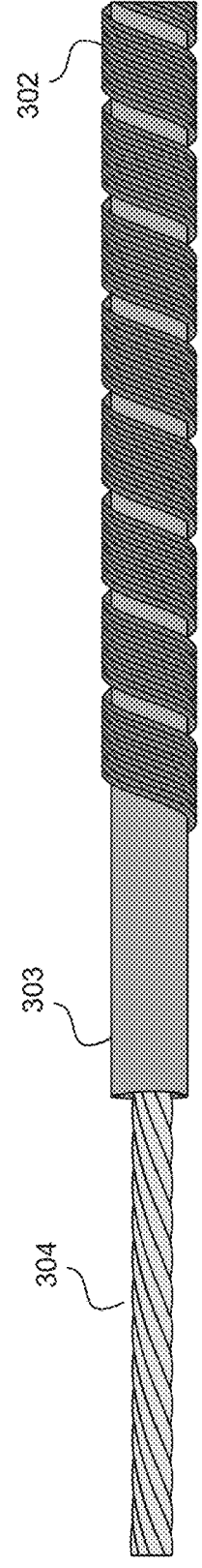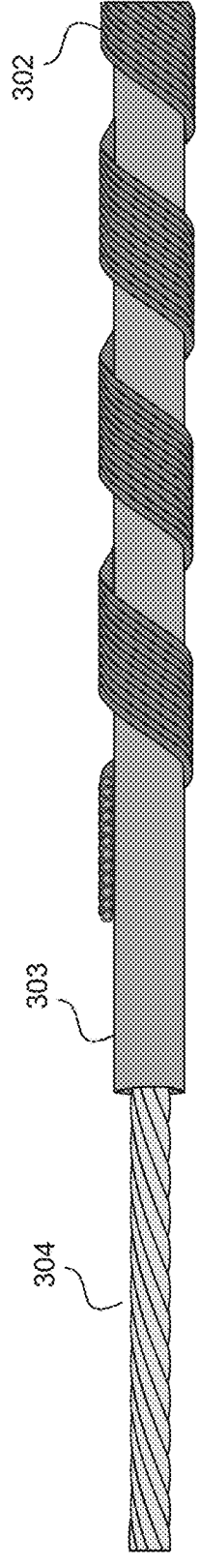
FIG. 6B
FIG. 6C
FIG. 6D

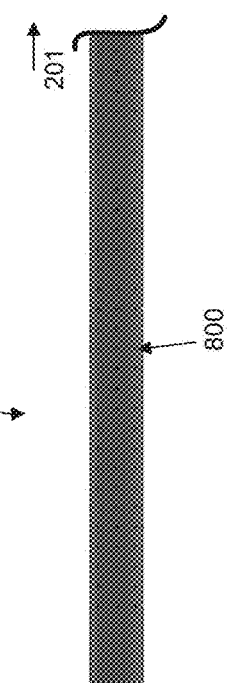
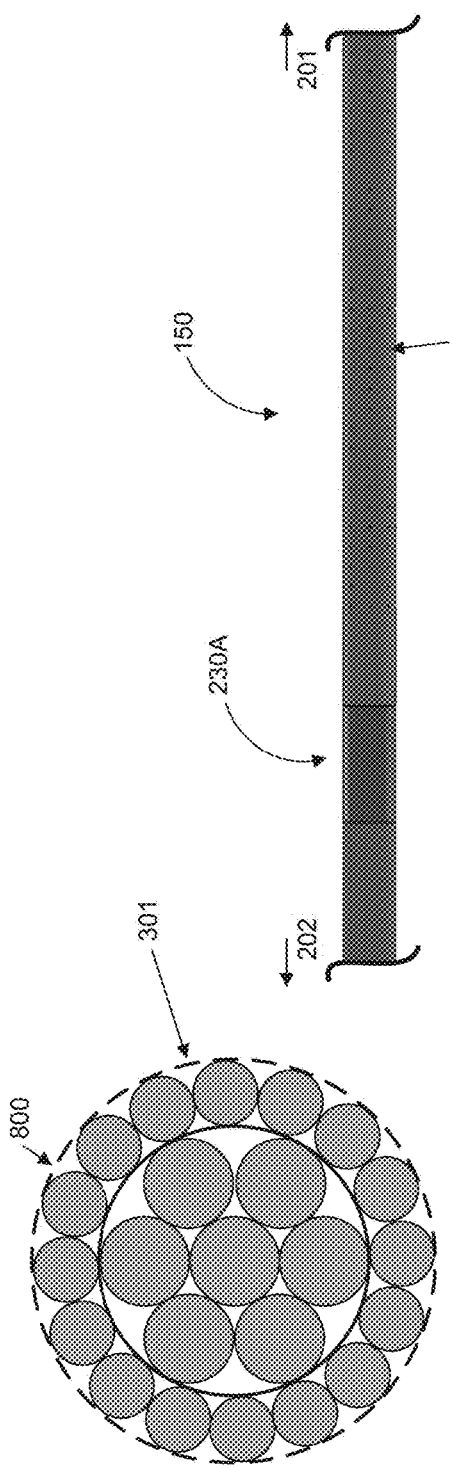
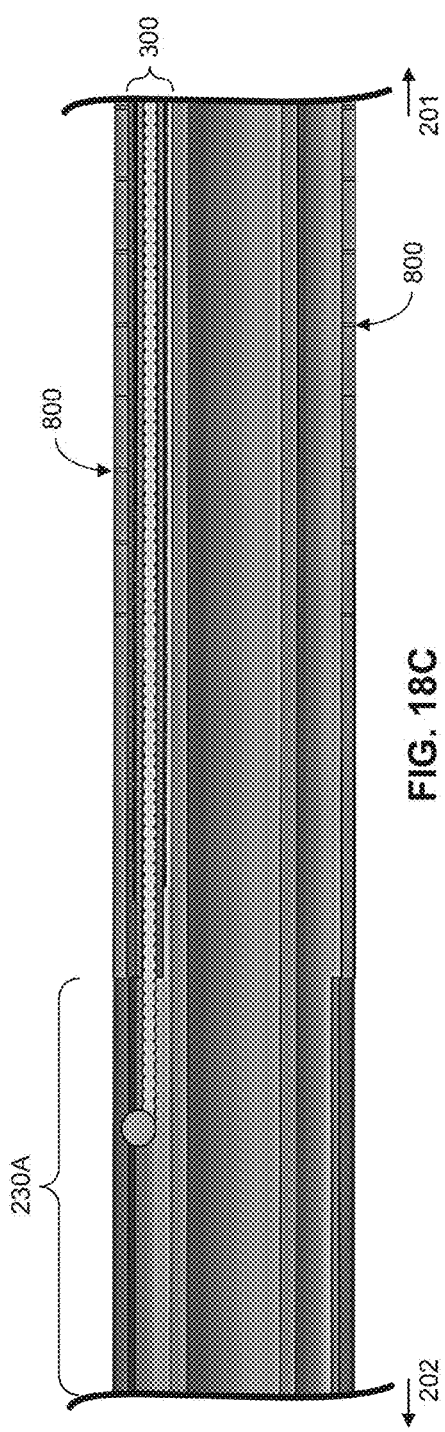

MRI COMPATIBLE MEDICAL DEVICES

RELATED APPLICATIONS

This application claims priority to U.S. provisional application No. 61/987,891, the disclosure of which is incorporated herein in its entirety by reference thereto.

BACKGROUND

Field of the Invention

The systems and methods disclosed herein relate to medical devices that can be used with magnetic resonance imaging procedures. More specifically, the systems and methods relate to medical devices with electromagnetic interference shielding.

Brief Summary

In one embodiment, a medical device for conducting an electrical nerve stimulation signal is provided. The medical device comprises an elongate member having a proximal end and a distal end. An electrical contact is disposed at the proximal end of the elongate member. An electrode is disposed at the distal end of the elongate member. A cable extending along the elongate member electrically connects the electrical contact to the electrode. The cable comprises three concentric layers which include: a first layer comprising an inner conductor, a second layer comprising an inner insulator, and a third layer comprising an outer conductor. The second layer is configured to electrically isolate the first layer from the third layer. A connecting member that circumferentially surrounds the elongate member is provided between the electrical contact and the electrode. The connecting member is configured to ground the third layer.

BRIEF DESCRIPTION OF THE DRAWINGS/FIGURES

FIG. 6B is a side view of a cable with a coiled third layer according to one embodiment.

FIG. 6C is a side view of a coiled third layer of a different pitch than the pitch of the third layers in FIGS. 6A and 6D according to one embodiment.

FIG. 6D is a side view of a coiled third layer of a different pitch than in FIGS. 6B and 6C according to one embodiment.

FIG. 15 shows the distal end with several components removed for discussion purposes.

FIG. 18A is a cross-sectional view of a cable with microscopic holes in the outer insulation layer according to one embodiment.

FIG. 18B is a side view of an elongate member of a lead with microscopic holes according to one embodiment.

FIG. 18C is a longitudinal cross-sectional view of the elongate member of the lead with microscopic holes according to one embodiment.

DETAILED DESCRIPTION

The following detailed description is merely exemplary in nature and is not intended to limit the invention or the application and uses of the invention.

Magnetic resonance imaging (MRI) is a non-invasive imaging tool that allows caregivers to study both structure and function of the human body. Its non-ionizing method of imaging and ability to produce detailed image slices provide advantages over other types of imaging, such as X-ray imaging. It is used in the treatment and diagnosis of many medical conditions, including cardiac and neurological ailments.

During an MRI procedure, three types of energy are produced by the MRI scanner: a static magnetic field ($B_0$), gradient magnetic fields ($B_1$), and radio-frequency pulses. A core magnet found in the MRI scanner emits the static magnetic field. The strength of this magnetic field typically ranges from 0.3 Tesla to 3 Tesla, but may be as high as 6 Tesla. The purpose of this static field is to align the spins of protons of hydrogen atoms in the body, which are normally in unaligned, random spins.

In order to target a specific area of the body, gradient coils are placed within the MRI scanner. The gradient coils produce gradient magnetic fields which vary the strength of the $B_0$. Thus, different portions of the body are subject to magnetic fields of different strengths. The gradient magnetic fields are switched on and off during imaging. These gradient fields affect the protons' resonance frequency. To image a certain area of the body, a radio frequency pulse with a certain frequency is emitted. The hydrogen protons having a resonant frequency matching the emitted frequency absorb the energy, causing their aligned spins to reverse. Once the radio frequency pulse is turned off, the protons revert to their previous state, emitting an energy signal that is picked up by receiver coils in the MRI scanner. This signal is transferred to a computer that renders it into an image.

The electromagnetic energy produced during MRI, especially the gradient magnetic fields and the RF pulses, raise safety concerns. This is especially true when MRI is used in conjunction with certain types of medical devices due to the possibility of electromagnetic interference. For example, the radio frequency pulses produced by the MRI scanner may cause induced and undesirable currents in implantable medical devices or catheters/guidewires that are for carrying electrical signal. These induced currents can cause elevated temperatures at the tip of the device and damage to the medical device.

Figure 1:
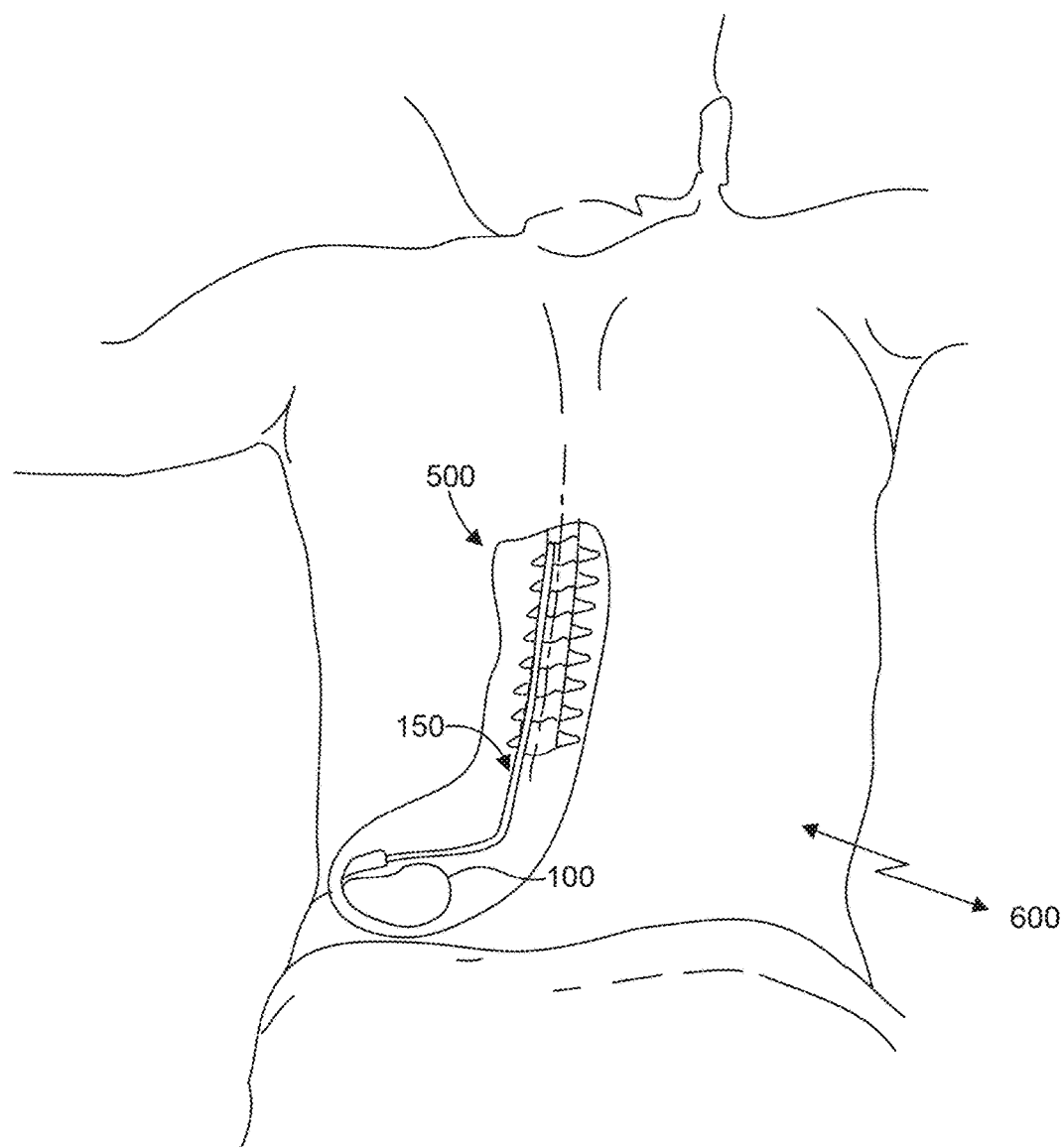
FIG. 1 shows a spinal cord stimulation (SCS) system with a pulse generator and a lead.

One type of implantable medical device that may be affected by MRI are leads. Leads are used with electrical stimulators such as cardiac pacemakers, deep brain stimulation (DBS) systems, and spinal cord stimulation (SCS) systems. SCS, DBS, and pacemaker systems are used to alleviate pain or regulate tissue functions in a variety of medical conditions, such as chronic back pain, Parkinson's disease, or cardiac conditions. For exemplary purposes only, a SCS system is shown in FIG. 1. The system of FIG. 1 consists of an implantable pulse generator 100, and an implantable electrical lead 150. The pulse generator 100 may be implanted near the spinal cord of the patient. The lead 150 is electrically connected to the pulse generator 100, and is typically implanted in the patient's epidural space along the patient's spinal cord. An electrical therapy signal generated by the pulse generator 100 is delivered to target neural tissue via the implantable electrical lead 150.

Another type of medical device that may be affected by MRI are catheters and guidewires. Catheters and guidewires are helpful and sometimes necessary accessories used to guide and introduce other types of medical devices into a body area of interest. Additionally, they may be used to access and study an anatomical area. For example, in a transfemoral catherization, a catheter is introduced from a vein in the leg into the heart to study the arteries and veins of a patient's heart.

Many times, MRI can enhance the placement of these medical devices. Additionally, patients with these types of implanted medical devices may need an MRI to diagnose and treat other conditions. Because MRI is a useful imaging tool with advantages over other types of imaging procedures, medical devices that can be used with MRI procedures are desirable. Additionally, it is desirable to provide these medical devices without increasing the cost of manufacturing or changing the mechanical characteristics of the device.

FIG. 1 illustrates a spinal cord stimulator (SCS) system 500 that may be implanted into a patient. The SCS system includes an implantable pulse generator 100 electrically connected to at least one lead 150. Lead 150 is implanted in the patient's epidural space along the spinal cord. While FIG. 1 shows only one lead, there may be multiple leads connected to the pulse generator.

The implantable pulse generator 100 may be implanted in the body near the upper buttocks, abdomen (not shown), or pectoral region (not shown). The implantable pulse generator 100 is for generating multiple electrical pulses, either simultaneously or in phase, each pulse having varying amplitudes and widths. The implantable pulse generator has a case and is powered through an internal power source, such as batteries, an external power source, or other means known in the art.

Figure 13:
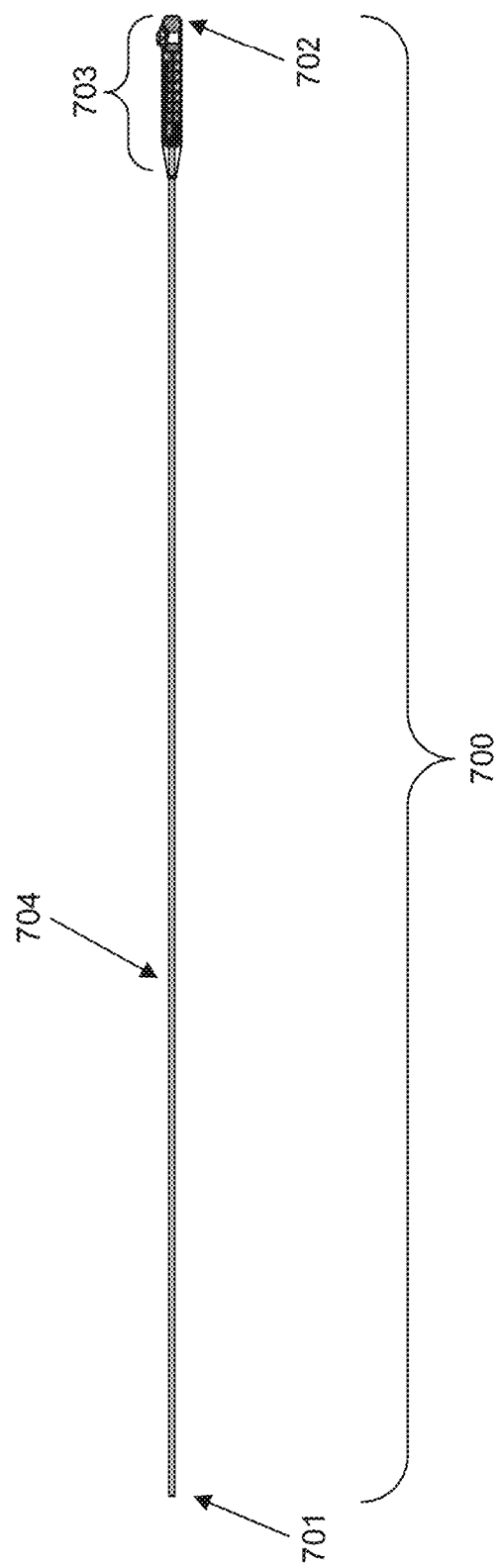
FIG. 13 is a side view of a lead extension according to one embodiment.

Lead 150 may be connected to the implantable pulse generator 100 either directly or through a lead extension 700, as shown in FIG. 13. When used without lead extension 700, lead 150 extends from the implantable pulse generator 100 to the spinal region, preferably terminating proximate to the desired region for treatment. When used with lead extension 700, lead 150 extends from a distal end 702 of lead extension 700 to the spinal region.

While lead 150 is shown as being used in a SCS system, lead 150 may also be used with other pulse generators, including but not limited to DBS systems or a cardiac pacemakers.

Figure 2:
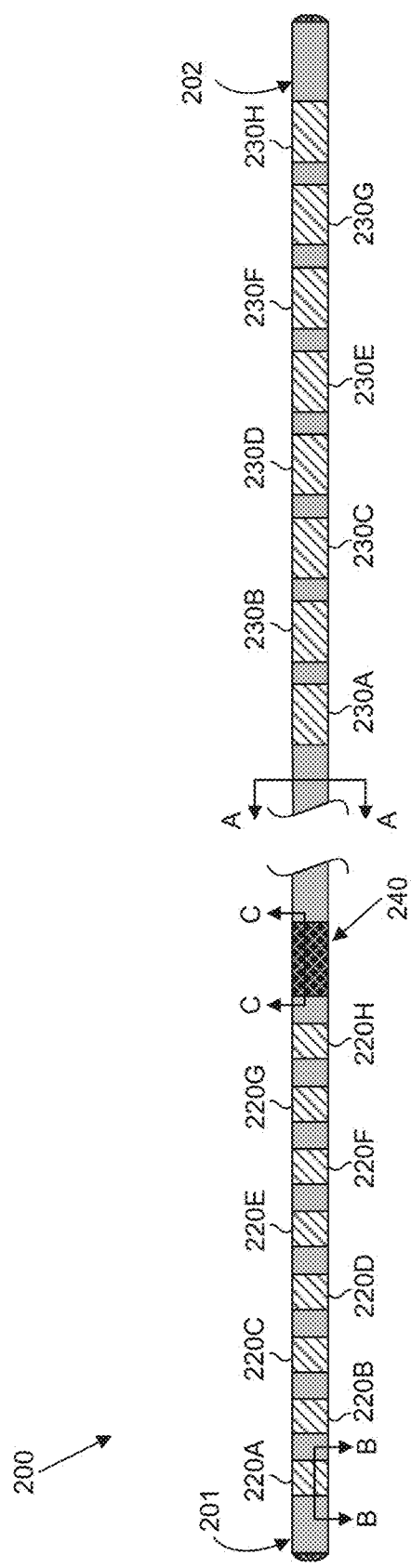
FIG. 2 is a side view of a shielded medical lead according to one embodiment.
Figure 3A:
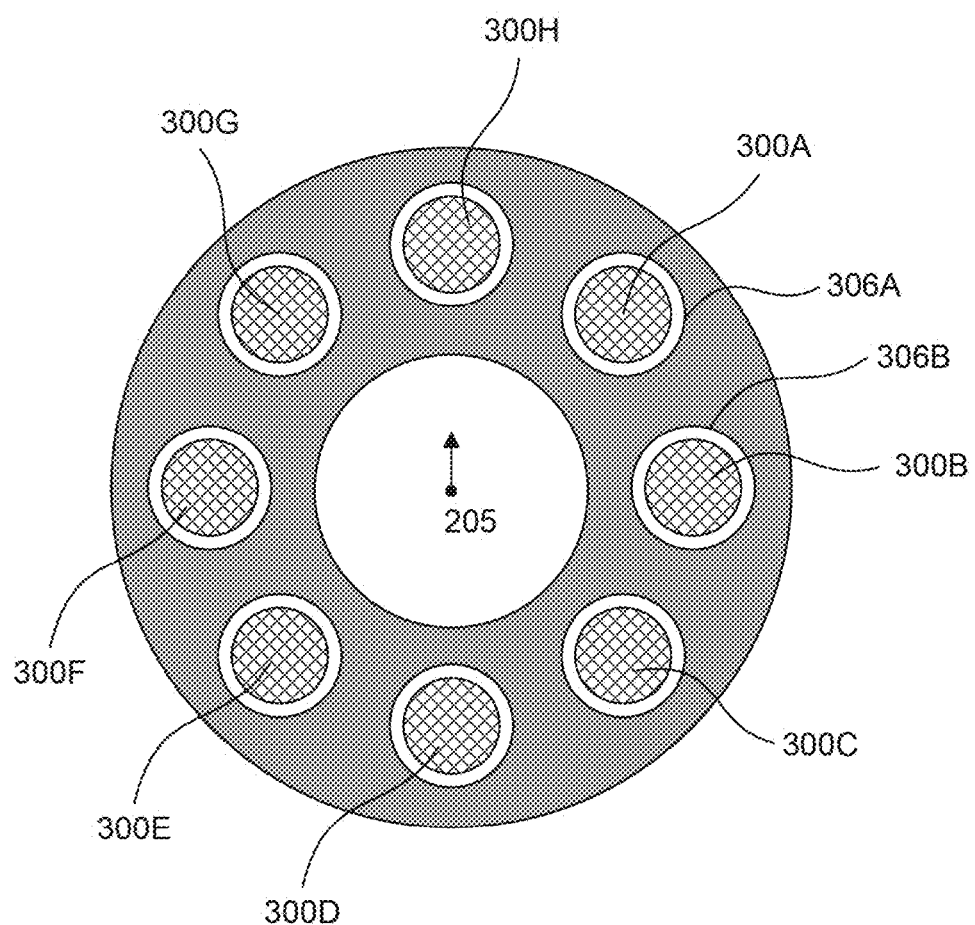
FIG. 3A is a cross-sectional view of the medical lead along line A-A in FIG. 2 according to one embodiment.

FIG. 2 shows an exemplary construction of lead 150 according to one embodiment. Lead 150 is comprised of an elongate member 200 with a proximal end 201 and a distal end 202. At least one electrical contact 220A is located at the proximal end 201 and at least one electrode 230A is located at the distal end. While FIG. 2 shows eight electrical contacts 220 (220A-H) and eight electrodes 230 (230A-H), the number of electrodes and electrical contacts may vary according to the tissue region to be treated and the therapy to be administered. Additionally, while electrodes 230 are shown as ring electrodes, the distal end of elongate member may have a paddle shape, allowing for other electrode configurations. FIG. 3A shows a cross-section of elongate member 200 along line A-A in FIG. 2. As seen in FIG. 3A, elongate member 200 comprises a plurality of cables 300. These cables extend along an interior portion of the elongate member, preferably from one electrical contact 220 to one electrode 230. As used herein, a "cable" may include a wire that is a composite of smaller wires. While eight cables 300A-H are shown in FIG. 3A, the number of cables can vary according to the tissue region to be treated and the electrical stimulation to be administered. In one embodiment, cables 300 are parallel to each other as they extend along the interior portion of the elongate member.

To accommodate these cables, elongate member 200 may have lumens 206 extending along a portion of its length. These lumens create channels for the cables and may be slightly larger than the cables themselves. Elongate member 200 may also optionally comprise a second lumen 205. This second lumen 205 may be used to introduce other medical devices inside the elongate member 200, including but not limited to stylets (not shown) that may help with device maneuvering and placement. This lumen 205 may be located at the radial center of the elongate member, as shown in FIG. 3A, or off-center. Elongate member 200 may also have other lumens and layers not shown, including but not limited to a stiffening layer of polyimide or similar material.

Figure 3B:
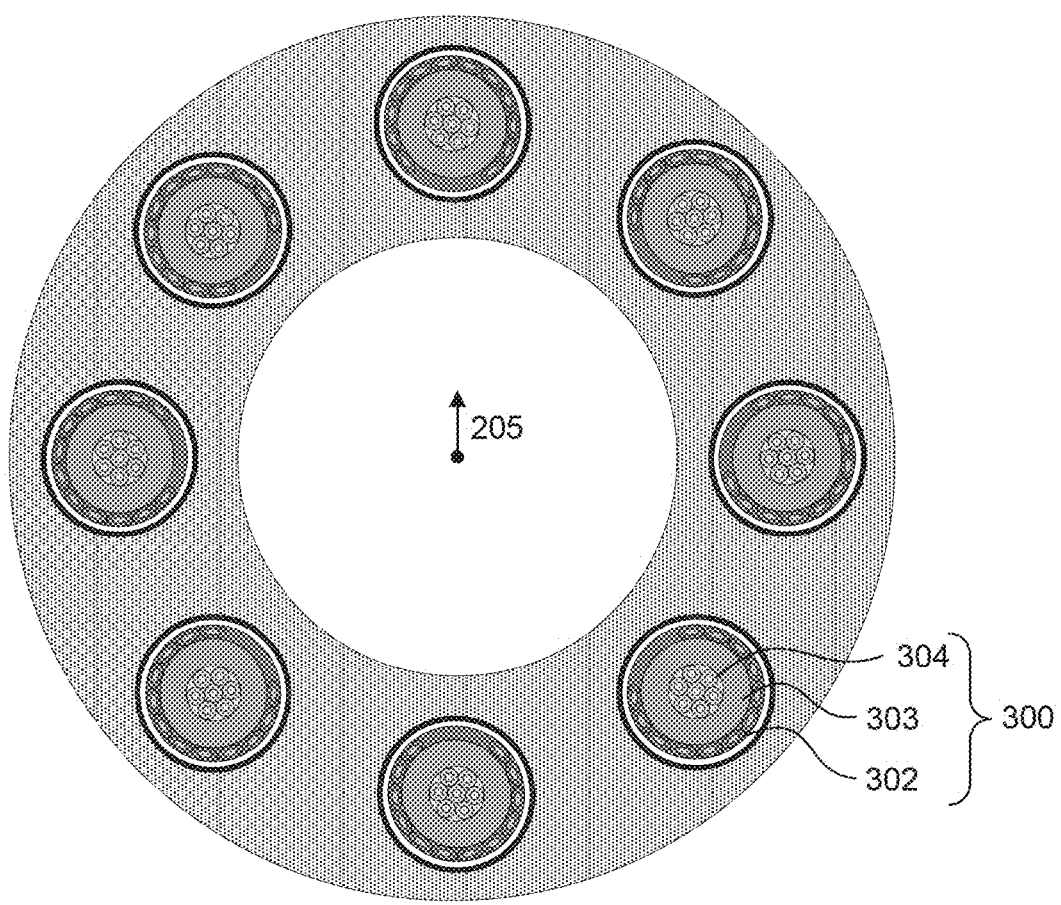
FIG. 3B is a cross-sectional view of medical lead along line A-A in FIG. 2 according to one embodiment.
Figure 4A:
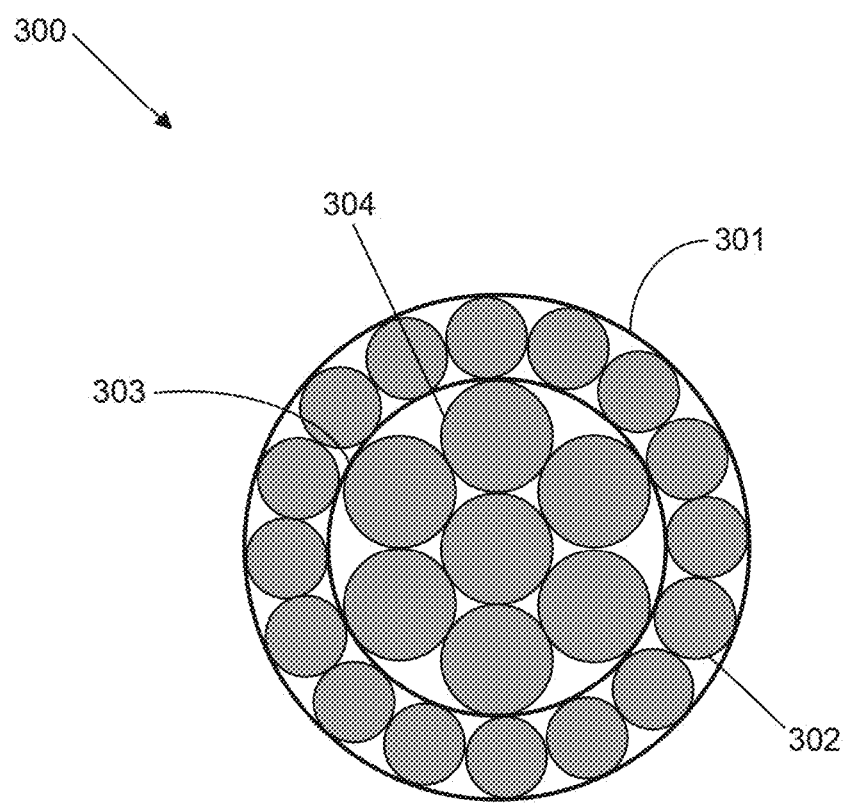
FIG. 4A is a cross-sectional view of a cable with four layers according to one embodiment.

The composition of cable 300 will now be discussed. As shown in FIG. 4A, in one embodiment, each cable 300 is comprised of four concentric layers: the first layer, the second layer, third layer, and the fourth layer. As used herein, "concentric" includes layers having the same radial center. However, each cable 300 may comprise other concentric layers not shown in FIG. 4A, such as other conducting or insulting layers. Additionally, as will be discussed later in relation to FIG. 3B, in one embodiment, each cable 300 may have fewer than four concentric layers.

Figure 6A:
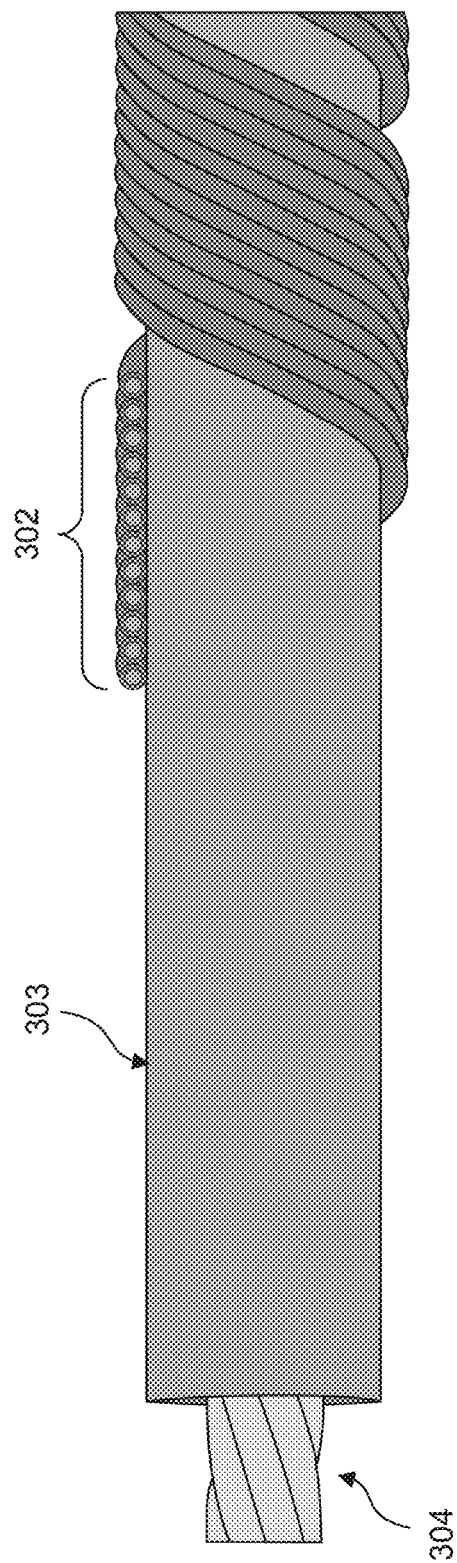
FIG. 6A is a side view of a cable with a wounded first layer and a coiled third layer according to one embodiment.

The first layer comprises inner conductor 304. Inner conductor 304 may be comprised of individual wire filars. These wire filars may be braided or wound together or they can run in parallel to each other. While FIG. 4A shows seven individual wire filars, the number of individual wire filars may vary depending on design requirements such as device size and electrical conducting needs. For example, in an inner conductor with individual wire filars braided together, the number of filars can be varied to change the impedance of the inner conductor. Additionally, while FIG. 4A shows a certain configuration of individual filars, one filar surrounded by six filars, other configurations may be used, such as helically would, co-radial individual filars. In this co-radial configuration, inner conductor 304 resembles a braided sheath with a center lumen. Alternatively, instead of being comprised of individual filars, the inner conductor may be comprised of a single braided or non-braided tube. FIG. 6A shows an embodiment where the individual filars of the inner conductor 304 are wound or braided together.

The inner conductor 304 is comprised of a material for conducting electrical signal. In one embodiment, when inner conductor 304 is comprised of individual filars, the individual filars are comprised of MP355N LT wire with an Ag core. In one embodiment, the Ag content is present from about 10% to 28% by cross-sectional area. But it is understood that Ag content of about 10% to 44% may be acceptable. Other suitable conducting materials may also be used.

In one preferred embodiment, at least one individual wire filar of an inner conductor has a diameter of 0.0001 inches to 0.015 inches. However, the filars may have any diameter, depending on size and conductivity requirements of the lead design. In one embodiment, each individual wire filar of each inner conductor has a wire diameter between 0.0005 inches to 0.0015 inches. The individual wire filars in one cable may all have the same diameter, or they may have different diameters. Additionally, the individual wire filars of the inner conductor of one cable (300A) may or may not have the same diameter or be comprised of the same material as the wire filar of the inner conductor of another cable (300B).

Figure 5A:
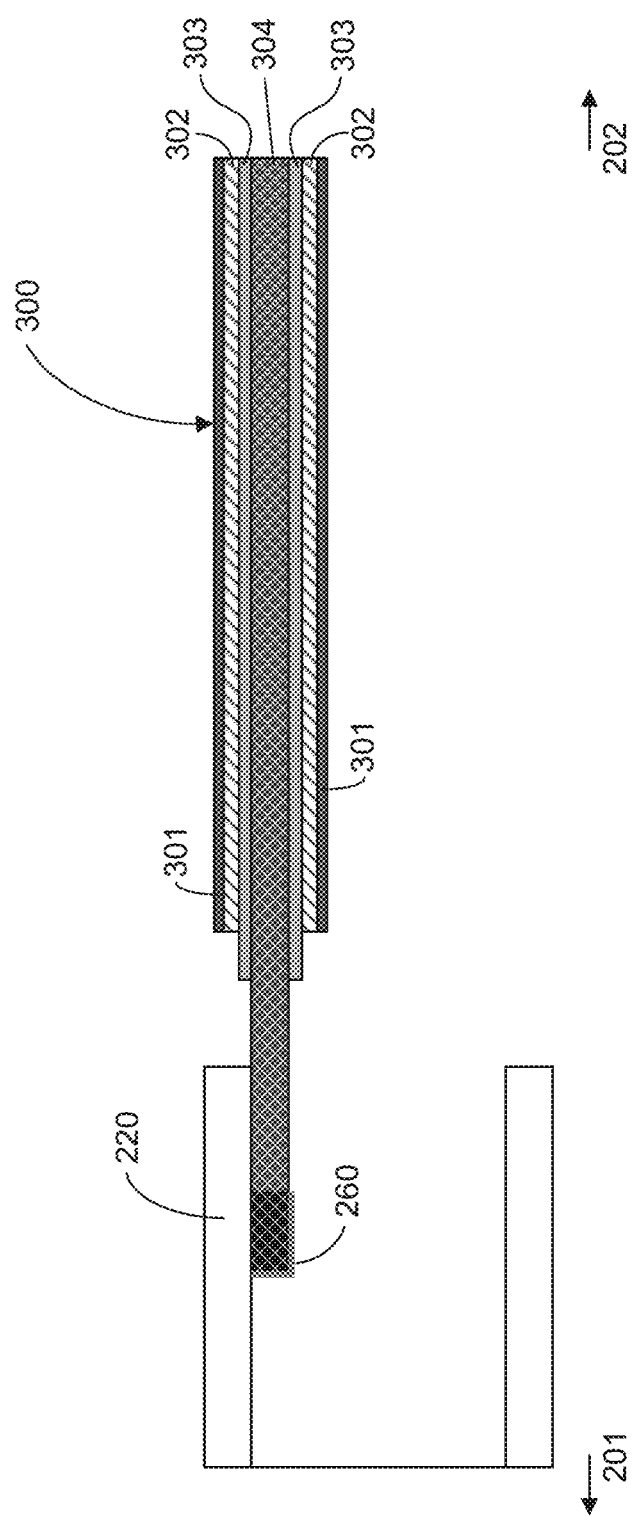
FIG. 5A is a schematic representation of a cable's proximal end in one embodiment where the cable has four layers according to one embodiment.

Inner conductor 304 of each cable 300 conducts the electrical signal generated by the pulse generator to the treatment area. FIG. 5A shows a partial longitudinal cross section of elongate member 200 along line B-B of FIG. 2. For simplicity, only the cable connected to the electrical contact is shown. Other portions of elongate member 200 are not shown.

As shown in FIG. 5A, the inner conductor 304 of each cable 300 is electrically connected to one of the electrical contacts 220 at the proximal end 201 of elongate member 200. Inner conductor 304 is also electrically connected to one electrode 230 at the distal end of the elongate member 200. These electrical connections are accomplished through welding pool 270, or other suitable methods including, but not limited to, crimping and soldering. Thus, the electrical signal is generated by the implantable pulse generator 100, transferred to the inner conductor through electrical contact 220, and delivered to the tissue at the distal end of elongate member 200 through the inner conductor 304 and electrode 230. As will be discussed below, in embodiments where the lead 150 is connected to the pulse generator 100 through a lead extension, the electrical signal is first transferred to the lead extension before it is relayed to the inner conductor.

Referring back to FIG. 4A, the second layer of cable 300 comprises an inner insulator 303. Inner insulator 303 preferentially extends along a length of each cable such that the second layer is configured to electrically isolate the first layer (comprising inner conductor 304) from the third layer (comprising outer conductor 302). One way to evaluate the electrical isolation between two conducting components is to measure the impedance between the components. Preferably, the second layer is designed such that the measured impedance between the first layer and the third layer is more than 1 MOhms.

Figure 5B:
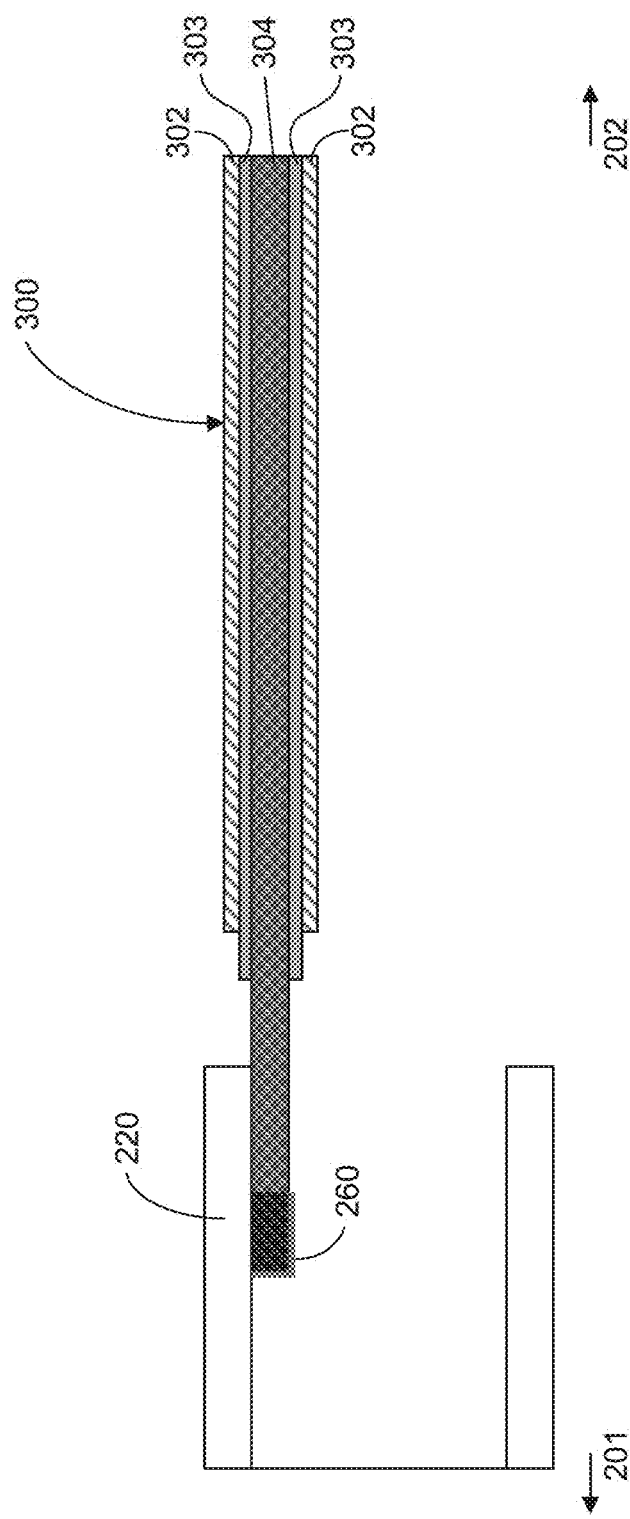
FIG. 5B is a schematic representation of a cable's proximal end in one embodiment where the cable has three layers according to one embodiment.

In one embodiment, as shown in FIGS. 5A and 5B, inner insulator 303 does not extend the full length of the cable 300. Rather, the inner conductor 304 extends further than the inner insulator 303 in both the proximal and distal directions in order to electrically connect to the electrical contact 220 and the electrode 230.

Inner insulator 303 may be comprised of any non-conductive material. In one embodiment, ethylene tetrafluoroethylene (EFTE) is used. ETFE is known for its excellent electrical radiation resistance properties, such as its high dielectric strength. However, inner insulator 303 may be comprised of other non-conductive materials or a composite of materials having suitable insulating properties.

In one embodiment, the inner insulator 303 has a wall thickness of 0.0001 inches to 0.025 inches, preferably from 0.0001 to 0.002, and more preferably from 0.00075 to 0.002 inches. These ranges provide efficient electrical isolation while retaining desirable lead profile size and pliability. Lead profile size and pliability are characteristics that, as discussed later, affect the performance of many medical devices, such as leads. While certain ranges are given above, the wall thickness may be within other ranges due to the operating and performance requirements of the lead.

The third layer will now be discussed. Referring back to FIG. 4A, the third layer of cable 300 comprises an outer conductor 302. Outer conductor 302 is configured to reduce the electromagnetic interference of an external source of electromagnetic energy (like the MRI scanner 600 in FIG. 1) on the inner conductor 304.

In one embodiment, outer conductor 302 is comprised of at least one individual wire filar. It is preferably comprised of twelve individual wire filars. The number of individual wire filars in each outer conductor, however, may vary according to lead design. Additionally, these filars may be parallel to each other or they may be helically wound as a coil or woven into a braid.

FIG. 6A shows an embodiment where the outer conductor 302 is helically wound as a coil. The pitch of the coil wound may be varied as needed for lead flexibility and shielding requirements. FIGS. 6B-6D show outer conductors with varying pitches, from being more closely wounded (FIG. 6B) to more loosely wounded (FIG. 6D).

Figure 7A:
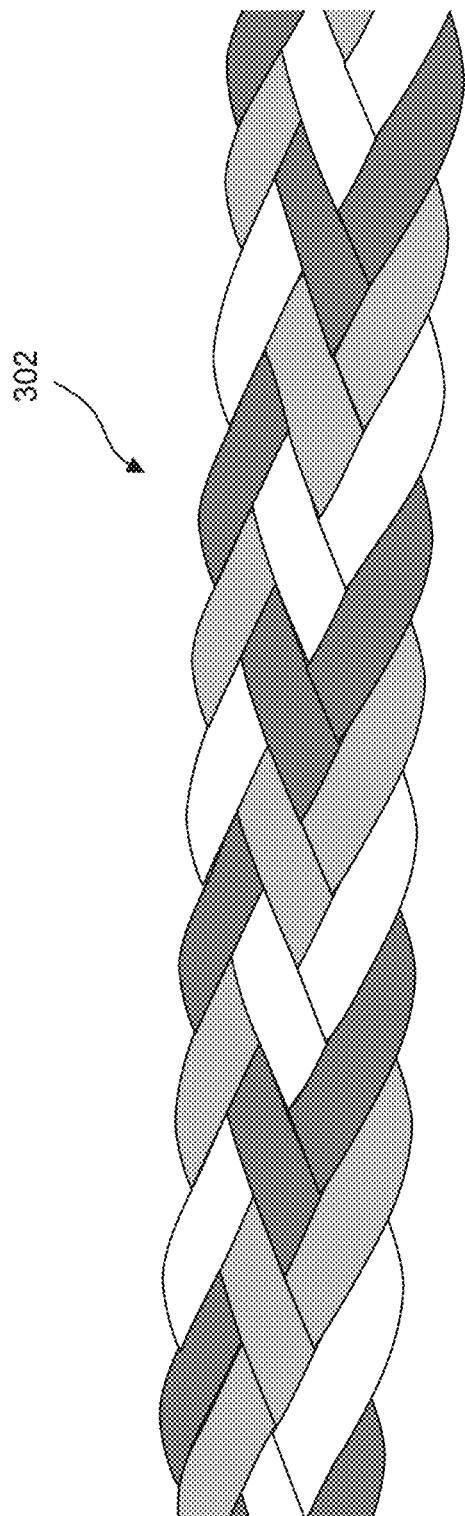
FIG. 7A is a side view of a braided third layer with a higher pitch than the pitch of the braided third layer in FIG. 7B according to one embodiment.
Figure 7B:
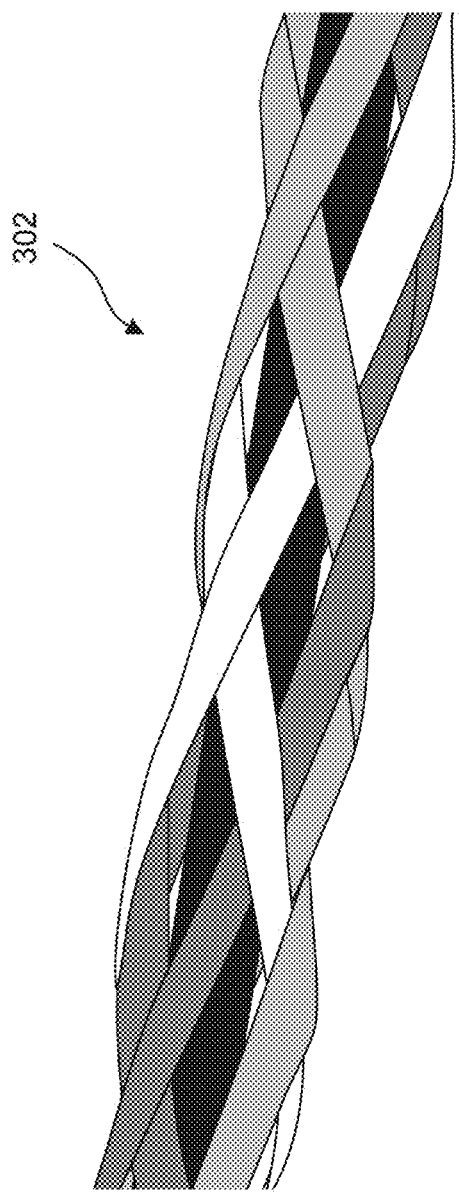
FIG. 7B is a side view of a braided third layer with a lower pitch than the pitch of the braided third layer in FIG. 7A according to one embodiment.

FIG. 7A shows an embodiment where the outer conductor 302 is braided. As with the helically wound coil construction, the braid may be of various pitches or densities. FIG. 7A shows an outer conductor braid with a relatively high pitch. FIG. 7B shows an outer conductor braid with a lower pitch or density than the pitch shown in FIG. 7A. In some embodiments with a lower density outer conductor braid, the other layers of the lead, such as the inner insulator 303 may be visible through the gaps in the braid of the outer conductor. For example, in FIG. 7B, the inner insulator 303 is visible through the gaps of the braid.

Figure 8A:
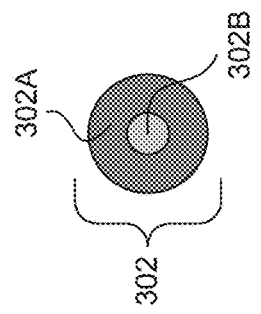
FIG. 8A is a cross-sectional view of an individual wire filar of the third layer according to one embodiment.
Figure 8B:
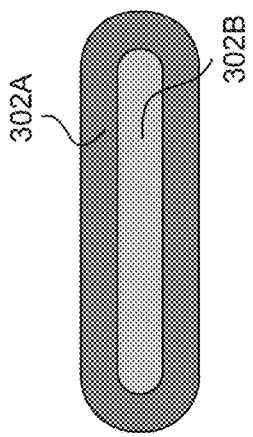
FIG. 8B is another cross-sectional view of an individual wire filar of the third layer according to one embodiment.
Figure 8C:
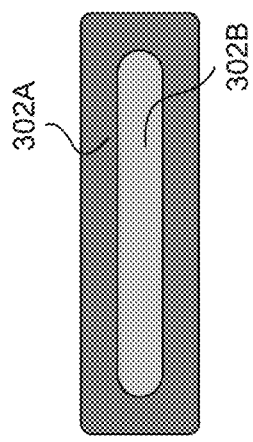
FIG. 8C is another cross-sectional view of an individual wire filar of the third layer according to one embodiment.
Figure 8D:
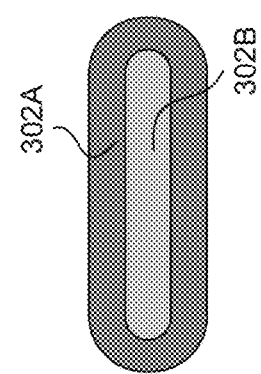
FIG. 8D is another cross-sectional view of an individual wire filar of the third layer according to one embodiment.

The individual wire filars of the outer conductor 302 may be comprised of a similar material as the individual wire filars of the inner conductor 304 or they may be comprised of a different material. In one embodiment, the individual wire filars of the outer conductor are made of MP35N LT. In one embodiment, the individual wire filars may comprise more than one material. For example, as shown in FIG. 8A, the individual wire filar may have an outer layer 302A and inner core 302B. Outer layer 302A may comprise one or more bio-compatible materials having high corrosion resistant capabilities and inner core 302B may comprise one or more highly conductive materials. As a non-limiting example, an individual wire filar may have an MP35N outer layer with an Ag inner core. Other combinations of materials may be used including, but not limited to, MP35N, tantalum, palladium, stainless steel, platinum, nitinol and similar materials for the outer layer and silver, copper, gold, palladium, tantalum, platinum, or nickel for the inner core. However, other suitable materials are also envisioned.

The individual wire filars of the outer conductor 302 may have certain cross-sectional shapes. FIGS. 8A-8D show non-limiting examples of different cross sections, including circular and rectangular cross-sections.

Additionally, at least one individual wire filar of the outer conductor 302 may have a diameter between 0.0003 inches to 0.013 inches. This diameter may be selected according to design requirements of the specific lead such overall lead diameter and electrical conductivity requirements to provide effective shielding. All individual wire filars in one cable 300 may have the same diameter, or they may have different diameters. Additionally, the individual wire filars of the outer conductor 302 of one cable may or may not be of the same size and comprised of the same material as the wire filar of the outer conductor of another cable.

In relation to the diameter of the wire filars of the inner conductor 304, the wire filar of the outer conductor may have similar or different diameters. Thus, for example, the filars of inner conductor 304 may have a different diameter than the filars of outer conductor 302, as depicted in FIG. 4A, where the filars of inner conductor 304 have a larger diameter than the filars of outer conductor 302.

Outer conductor 302, like inner conductor 304, may also comprise a single non-braided tube. An example of a single non-braided tube is one manufactured as a laser cut tube. Cuts or other physical modifications may be present in the tube to alter its underlying physical characteristics. For example, a spiral cut along the tube's length may increase the flexibility of the tube over its length. Other types of cuts are envisioned as well.

Like inner conductor 304, outer conductor 302 is also electrically conductive. The inner insulator 303 of the second layer substantially electrically isolates the inner conductor 304 of the first layer from the outer conductor 302. Thus, the inner conductor 304 is essentially unaffected by current in outer conductor 302 and the outer conductor 302 is essentially unaffected by current in inner conductor 304. Accordingly, outer conductor 302 acts as a shield for inner conductor 304 by absorbing the electromagnetic energy produced by the MRI scanner. Because the current of the inner conductor 304 is unaffected, heating at the electrodes 230 and potential of electrical damage to the device due to induced currents is significantly reduced.

Different MRI procedures may require different static magnetic fields. The strength of the static magnetic field, in turn, affects the RF frequencies used in that procedure. Thus, a device that may be safely used with one type of MRI procedure may not be safely used with another. In other words, the RF frequencies that a medical device can be used with is affected by the outer conductor's shielding capability.

One way to characterize the shielding capability of the outer conductor is by referring to the RF frequencies the device may be safely used with. Embodiments disclosed herein are configured to withstand RF frequencies used with a wide range of static magnetic fields. These include but are not limited to RF frequencies of 64 MHz (used in a 1.5 Tesla static field) to 128 MHz (used in a 3 Tesla static field), and up to 256 MHz (used in a 6 Tesla static field).

Another way to characterize the shielding capability of the outer conductor is to directly measure how much electromagnetic energy is absorbed by the outer conductor. In one embodiment, the outer conductor is configured to absorb about 3 decibels (dB) to 30 dB of electromagnetic energy.

Referring back to FIG. 4A, cable 300 has a fourth layer comprised of outer insulator 301. Outer insulator 301 is configured to substantially electrically isolate the outer conductor 302 from the surroundings of cable 300, which includes other portions of the elongate member 200. The outer insulator 301 may also be used to protect the outer conductor 302. For example, it may reduce or prevent damage to the outer conductor 302 when the outer conductor 302 is inserted into a lead body by preventing the unraveling of the coil or braid construction. FIGS. 10A and 10C also show cables 300 with outer insulators 301. Outer insulator 301 may extend along the entire length of the cable or it may extend along only a portion of the cable. In one embodiment, as shown, in FIG. 10B, the outer insulator 301 is present only near the ends of the cable. This helps to retain the outer conductor and adds to the stability of the lead construction. Additionally, it may also provide additional insulation. While the ends of the cable have been given as an exemplary location, it is envisioned that 301 may be located at other locations of the cable in order to increase stability at that location. For example, in addition to or instead of being present near the cable ends, the outer insulator may be present near the cable's center portion.

Outer insulator 301 is comprised of any suitable non-conductive material. This material may be the same material used for inner insulator 303. Alternatively, it may be a different non-conductive material. In one embodiment, this material is ETFE. In another embodiment, it may be comprised of heat shrink polymer tubing. Materials used as the outer insulator 301 may ground the outer conductor through the outer insulator itself.

Figure 9A:
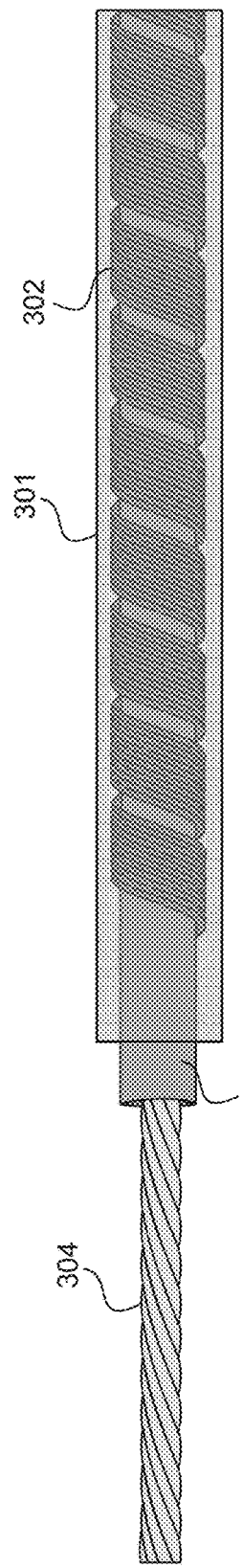
FIG. 9A is a side view of a cable with four layers according to one embodiment.
Figure 9B:
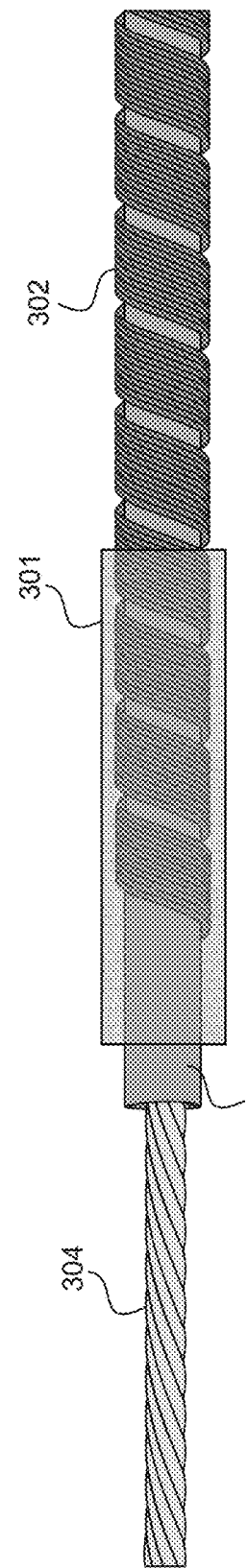
FIG. 9B is a side view of a cable with a fourth layer that extends along only a portion of the cable according to one embodiment.
Figure 9C:
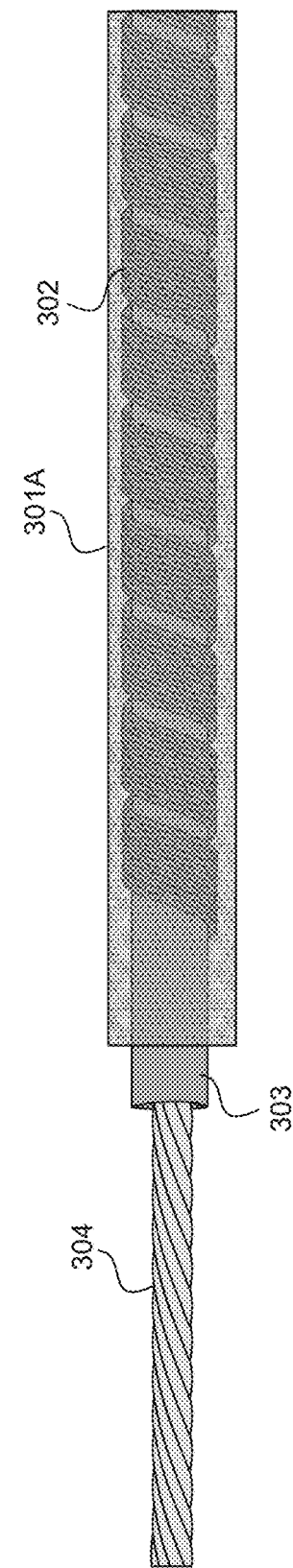
FIG. 9C is a side view of a cable with a fourth layer comprised of a dissipative material according to one embodiment.

For example, in one embodiment shown in FIG. 9C, portions of the outer insulator 301 may be comprised of a static dissipative material 301A which may help dissipate any excess charge buildup in the outer conductor layer and help to ground the outer conductor. This material may include particles of low density so as to not be completely conductive. In embodiments including the static dissipative material 301A, it is preferable that the portion of the outer insulator 301 comprising the static dissipative material is not present near the electrodes 230 or the electrical contacts 220 of the lead 150 so that each electrode 230 remains electrically insulated from the other electrode and each electrical contact 220 remains electrically insulated from the other electrical contact. Thus, in embodiments where the entire outer insulator 301 is comprised of a static dissipative material, the outer insulator may not extend the full length of the lead 150.

In another embodiment, the structure of outer insulator 301 may be intentionally compromised in order to create an electrical short over at least a portion of the outer insulator 301. For example, as shown in FIG. 18A, microscopic holes 800 may be drilled into the outer insulator 301 to allow fluid to seep into the holes, thus creating a short. The drilling process may be done via a laser or other suitable methods. This is shown in FIG. 18A.

In one embodiment, the elongate member 200 of the lead 150 has similar microscopic holes 800 drilled into the elongate member. As shown in FIG. 18B, these holes 800 may be present over any specific portion of the lead 150. As a non-limiting example, these holes may be located in segments of the lead where the microscopic holes 800 in the outer insulator 301 are located.

FIG. 18C shows a longitudinal cross-section of the lead, in which the elongate member 200 of the lead 150 has microscopic holes 800 drilled into the elongate member 200. It is preferable, however, that holes 800 are not present near the electrodes 230 or the electrical contacts 220 of the lead 150 so that each electrode remains electrically insulated from the other electrode and each electrical contact remains electrically insulated from the other electrical contact.

In another embodiment, these microscopic holes 800 are filled in with a conductive material.

The outer insulator 301 may be comprised of one material or a combination of material. Additionally, the outer insulator may have different segments comprised of different materials or structures. For example, one segment may have holes 800 and another segment may not.

In one embodiment, the outer insulator 301 comprises a wall with a certain wall thickness. In relation to the wall thickness of the inner insulator, the wall thickness of the outer insulator 301 may be of the same or different thickness. In one embodiment, this wall thickness ranges from 0.0005 inches to 0.0015 inches. This range has been found to provide effective insulation properties. However, this work is not limited by this range and this range may vary depending on operation requirements of the lead, such as insulating requirements.

Embodiments disclosed herein are able to achieve effective electromagnetic shielding without sacrificing the needed pliability or profile size. Medical devices are often times designed to have certain pliability. For example, a device that is intended to reach a target area through a direct opening in the body (such as in coronary artery bypass surgery) does not require much flexibility. On the other hand, a device that is intended to reach a target area through a vein incorporates a certain amount of pliability. The pliability allows the caregiver to guide it through the vein path. Pliability also affects how a device handles flex fatigue stresses caused by cyclic loading. This characteristic is especially important in implanted devices, as these devices are subject to cyclic loading due to their long-term placement in the human body.

One way to characterize the pliability of a device is through its bending stiffness. For example, a medical lead intended for treatment of cardiac tissue may require a bending stiffness around $4 \times 10^{-5}$ lb-in$^2$. Other leads may require other stiffness values suitable for their intended applications.

Embodiments disclosed herein should have the requisite pliability such that the device is steerable and able to be guided through the intended tissue for placement. A device that is too rigid cannot be bent to navigate the path of insertion. On the other hand, a device that is too pliable cannot be steered due to its inability of translating movement from the proximal end to the distal end. Embodiments disclosed herein should also have the requisite pliability to meet industry acceptable flex fatigue testing standards for use in implantation.

Medical devices are also designed to have a certain profile size. The profile size of these devices may be limited due to the access opening and path. For example, a smaller incision for instrument access may be preferred due to decreased healing time and cosmetic concerns. Embodiments disclosed herein should have the requisite profile size for the intended medical application.

Many medical devices that are shielded from electromagnetic interference require the addition of extra layers placed over the entire device body in order to effectively shield the device. These additional layers alter the pliability of the device, such that it becomes harder to maneuver. The layers also increase the overall profile of the device. Thus, many shielded medical devices often times are not practical in application because of these issues. Additionally, changes in manufacturing processes that raise costs may be undesirable.

In elongate member 200, the inner conductor 304 of each cable 300 conducts the electric signal generated by the implantable pulse generator. The inner conductor 304 is shielded through inner insulator 303 and outer conductor 302. Thus, cables 300 are individually shielded and elongate member 200 does not require additional layers to shield it from electromagnetic interference.

The addition of the inner insulator 303 to each individual cable 300 does not substantially affect the overall profile or pliability of elongate member 200. In other words, an elongate member that is similar to elongate member 200 in every way except that it is does not have inner insulator 303 has similar pliability and diameter size to elongate member 200 (with inner insulator 303). Thus, embodiments disclosed herein are able to achieve effective electromagnetic shielding without sacrificing the needed pliability or profile size. Additionally, manufacturing costs are not substantially increased.

Figure 4B:
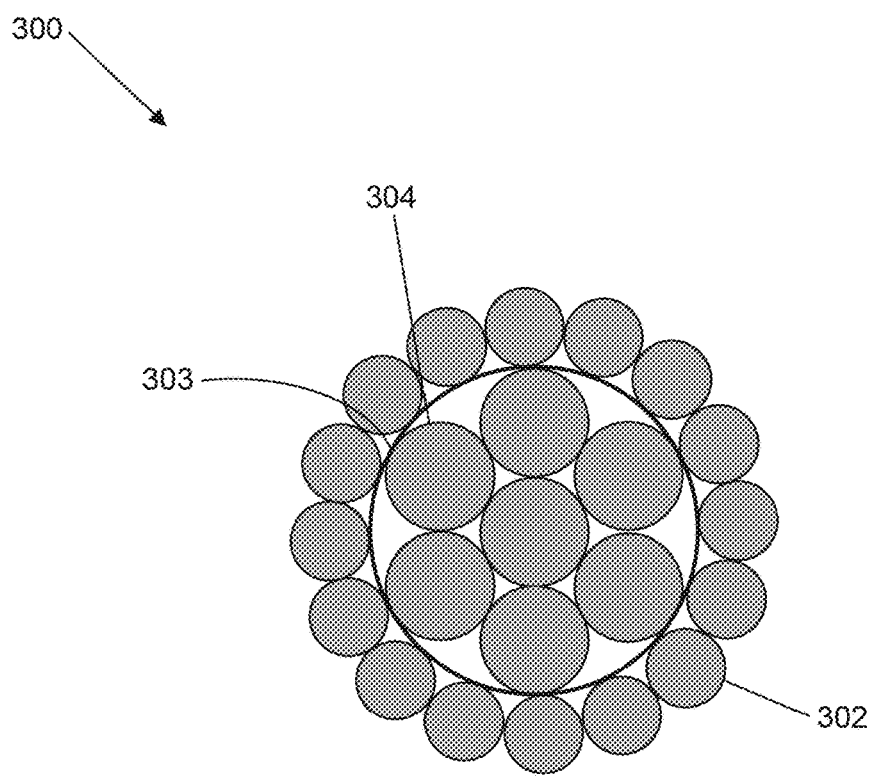
FIG. 4B is a cross-sectional view of a cable with three layers according to one embodiment.
Figure 4C:
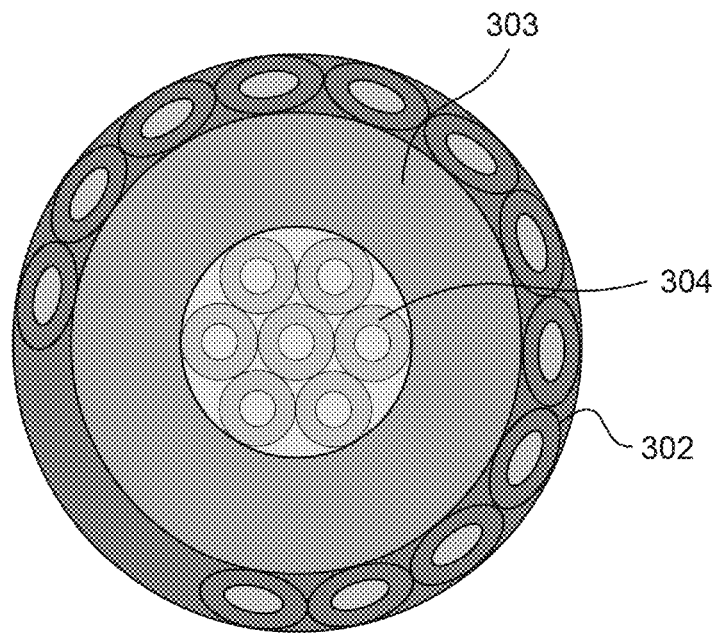
FIG. 4C is a cross-sectional view of a cable with three layers according to one embodiment.

Referring now to FIGS. 4B and 5B, in another embodiment, cable 300 does not have a fourth layer with outer insulator 301. FIG. 4C also shows a schematic of cable 300 without outer insulator 301. FIG. 3B shows a cross section of a lead 150 where all cables 300 have only the first three layers as in FIG. 5B. In this embodiment, as shown in FIG. 5B, the inner conductor 304 of cable 300 is still electrically connected to electrical contact 220 and electrode 230 and the inner insulator 303 is still configured to electrically isolate the inner conductor 304 from the outer conductor 302. In this embodiment, however, outer conductor 302 is exposed to other portions of the elongate member 200. Thus, in this embodiment, the outer conductor 302 has sufficient thickness and electrical properties such that it may function without being grounded through a separate path but is instead grounded through the surrounding body tissue.

Referring now to FIG. 2, elongate member 200 may also comprise a connecting member 240 located between the electrical contact and the electrode. In one embodiment, and as shown in FIG. 2, it is located adjacent to the last electrical contact 220H, on the distal side of elongate member 200. As shown in FIG. 2, connecting member may be in the form of a sleeve or ring located at a more distal position than the electrical contacts 220. Connecting member 240 may also of another shape or configuration different than the one shown in FIG. 2. In one embodiment, connecting member 240 mechanically connects and retains elongate member 200 to implantable pulse generator 100.

Connecting member 240 may also be electrically active or inactive. In embodiments with the outer insulator 301, as shown in FIGS. 4A and 5A, the connecting member 240 is preferably electrically inactive and comprised of non-conductive material. Similarly, in embodiments without the outer insulator 301 where the outer conductor 302 is grounded through the tissue, the connecting member is also preferably electrically inactive.

Figure 11C:
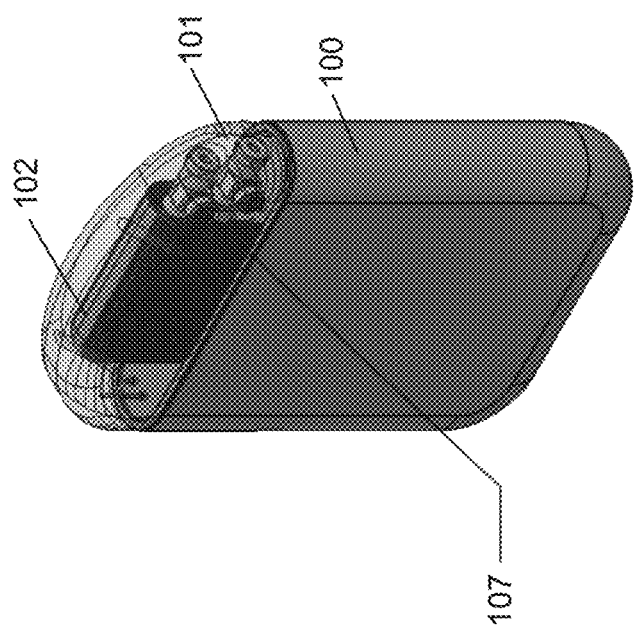
FIG. 11C is a perspective view of an implantable pulse generator with shielding materials in the header according to one embodiment.

As discussed above, the outer conductor may be grounded through the surrounding body tissue. Alternatively, the outer conductor 302 may be grounded through the implantable pulse generator 100 when there is no outer insulator 301. In this embodiment, the connecting member 240 is electrically active and comprised of conducting material. As shown in FIG. 11C, in one embodiment, the connecting member 240 is connected to a fastener 107 located in the header 101 of the implantable pulse generator. Fastener 107 may be a set screw block. While the overall structure of cable 300 and the proximal end of the cable is the same as described above (and shown in FIGS. 4B and 5B), the cross section of the elongate member 200 near the connecting member 240 may be different in this embodiment.

Figure 5C:
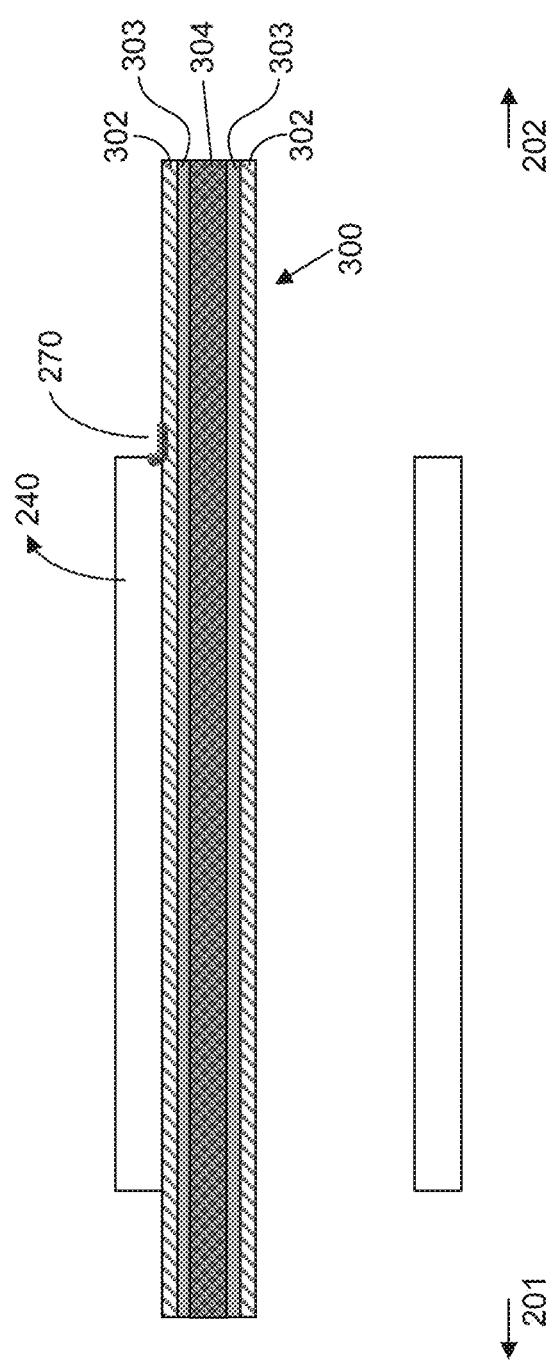
FIG. 5C is a schematic representation of the connecting member at the proximal end according to one embodiment.

FIG. 5C shows a cross section of elongate member 200 along line C-C in FIG. 2 for this embodiment. For simplicity, only one cable 300 is shown. Other portions of elongate member 200, such as lumen 205, are not shown. Here, the connecting member 240 is made of conducting material and is electrically coupled to the outer conductor of the cable. This is done through welding pool 270, but can include other methods including, but not limited to, crimping and soldering. Connecting member 240 is also electrically coupled (not shown) to a grounding material of the implantable pulse generator 100. In one embodiment, this material is the outer case of the implantable pulse generator 100.

Figure 10:
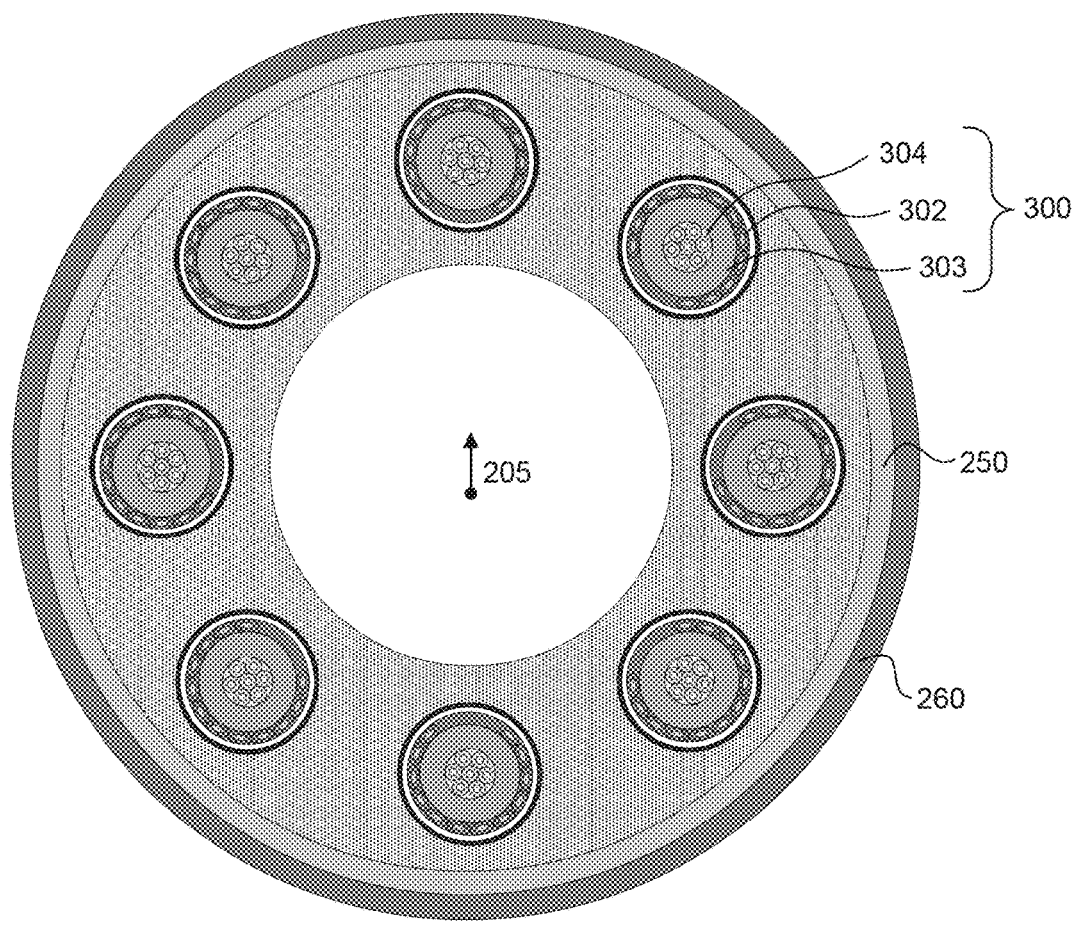
FIG. 10 is a cross-sectional view of a medical lead with additional shielding and insulating layers according to one embodiment.

In one embodiment, elongate member 200 may have additional layers not shown in FIG. 3A or 3B. For example, FIG. 10 shows a cross-section of one embodiment of elongate member 200 along line A-A of FIG. 2. As shown in FIG. 10, elongate member 200 comprises additional layers of shield material 250 and insulating material 260. These layers may radially encompass the lead 150 and extend along a portion of the length of the lead 150. Preferably, these layers do not extend along the entire length of the lead 150 due to the electrical contacts at the proximal end and the electrodes at the distal end. These layers may be used in situations where additional insulation and shielding is desired. FIG. 10 shows both additional layers being present, but one layer may be added without the other. For example, elongate member may have additional layer 250 but not layer 260. The materials that may be used for the shield layer 250 and insulating layer 260 may include the materials already discussed herein in relation to insulating and shielding materials.

In one embodiment, at least a segment of the shield layer 250 is comprised of a conductive tape 900. Preferably, the entire length of the shield layer 250 is comprised of conductive tape 900. FIG. 12B shows a lead 150 with conductive tape 900 as an additional shielding layer 250. Conductive tape 900 is wound around the lead 150 along a length of elongate member 200.

Figure 12A:
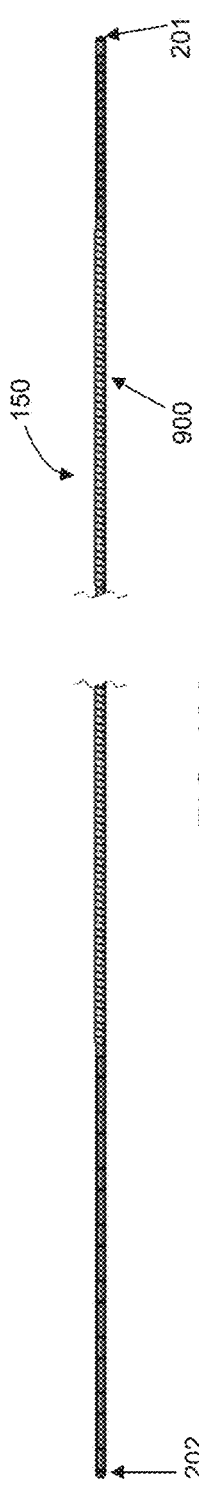
FIG. 12A is a side view of a lead with an additional shielding layer of conductive tape according to one embodiment.
Figure 12B:
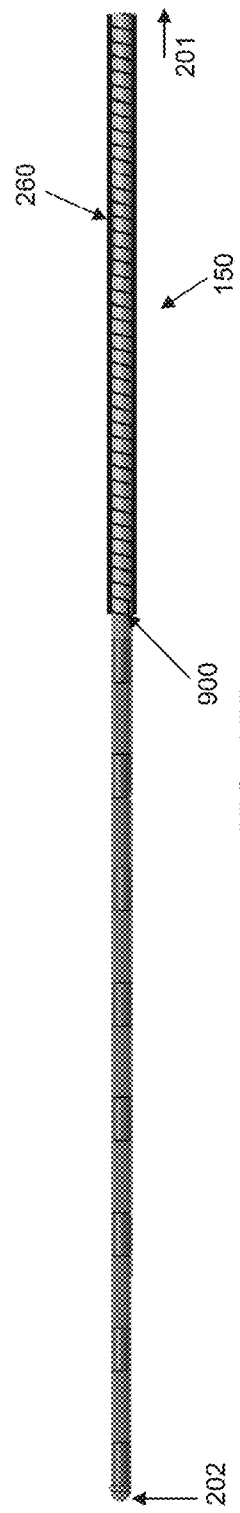
FIG. 12B is a side view of the lead of FIG. 12A with an additional insulation layer disposed over the conductive tape according to one embodiment.

As seen in FIG. 12A, the conductive tape does not extend all the way to the distal end or all the way to the proximal end of the elongate member because the electrodes and electrical contacts are located at those ends.

Figure 12C:
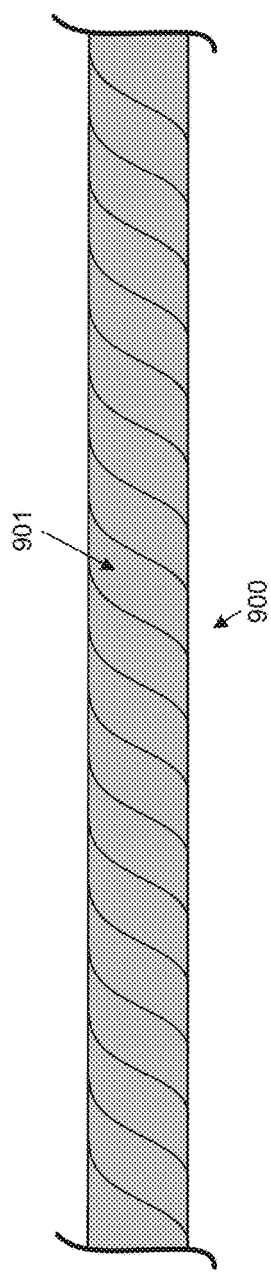
FIG. 12C is a detailed side view of the conductive tape according to one embodiment.

As shown, for example, in FIG. 12C, the conductive tape 900 is comprised of a conductive layer, such as metal coating 902 that is disposed on a polymer 901. The conductive tape 900 is then wound around the lead 150 such that the polymer 901 is on the side of the lead that interacts with the patient. The conductive layer 902 is on the inside of the lead.

This conductive tape 900 may act as an additional shield layer 250. In some embodiments, this conductive tape 900 is preferable because it may be easily wound around the lead and thus enhances ease of lead manufacturing.

Exemplary polymers used for the conductive tape 900 include polyurethane, silicone, and other bio-compatible polymers. Exemplary conductive materials include but are not limited to, and silver, copper, gold, palladium, tantalum, platinum, and nickel. Other suitable metals may also be used. Using conductive tape 900 in some embodiments may be advantageous because the conductive tape 900 may be easily wound around the lead 150. This may allow for improved ease of manufacturing.

Figure 12D:
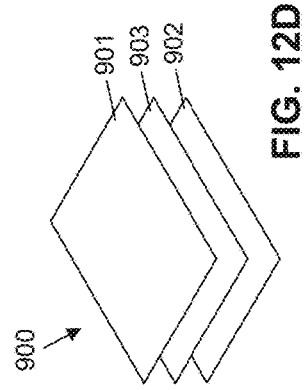
FIG. 12D is a schematic view of the layers of the conductive tape according to one embodiment.

In some embodiments and as shown in FIG. 12D, a base layer 903 may be used to improve the bonding of the polymer 901 to the conductive layer 902. In some embodiments, this base layer 903 is titanium. However, other suitable base layers that would improve the bond between the polymer 901 and the conductive layer 902 are also envisioned.

In some embodiments, and as shown in FIG. 12CB an insulating layer 260, as discussed above, may be placed over the polymer tape layer. For example, this layer may be comprised of heat shrink tubing.

Systems disclosed herein may also have shielding for portions of the system that are not on lead 150. For example, the system may also include a shielded lead extension.

As discussed above, lead extensions may be used in conjunction with the lead 150 to deliver the electrical stimulation to the treatment area. Lead extensions are used when the lead 150 is not long enough to extend from the pulse generator 100 to the treatment area. Thus, the concerns with MRI compatibility, which are discussed above in relation to leads, also apply to lead extensions. Both the lead and the lead extension should be MRI compatible.

Embodiments disclosed herein include lead extensions that are MRI-compatible. An exemplary lead extension is shown in FIG. 13. Lead extension 700 comprises a proximal end 701, an elongated body 704, and a distal end 702. A connecting portion 703 is located at the distal end. The proximal end 701 of the lead extension 700 connects directly to the implantable pulse generator 100. The distal end 702 of lead extension connects to the proximal end 201 of lead 150. Thus, the stimulation is generated by the implantable pulse generator 100, transferred to the proximal end 701 of the lead extension 700, translated down the elongated body 704 of lead extension 700, and transferred to the lead 150 through the connection of the distal end 702 of the lead extension 700 with the proximal end 201 of the lead 150.

Figure 14:
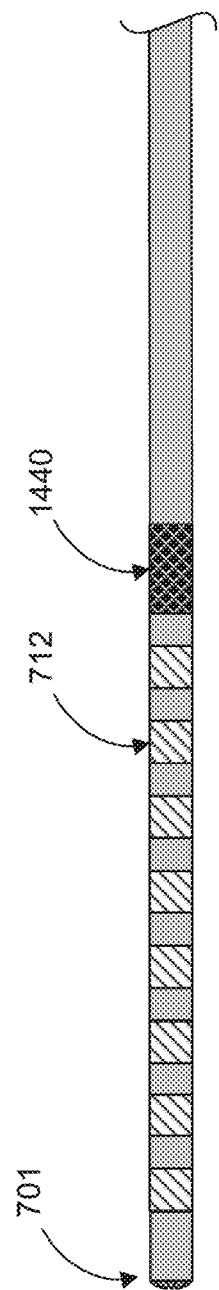
FIG. 14 is a side view of the proximal end of the lead extension of FIG. 13 according to one embodiment.

The proximal end 701 of lead extension 700 is shown in FIG. 14. It is similar to the proximal end 201 of lead 150 and contains at least one proximal electrical contact 712. In an embodiment, there are eight proximal electrical contacts. However, other numbers of electrical contacts are envisioned. There may also be a connecting member 1440 that is similar in structure and function to connecting member 240 discussed above. The discussion above regarding the proximal end of lead 150 is also applicable here.

Like lead 150, lead extension 700 also has cables extending along the elongated body 704. The cable connects at least one proximal electrical contact 712 to a distal electrical contact 705A on lead extension. In a one embodiment, there are eight proximal electrical contacts, eight distal electrical contacts, and eight cables.

Cables of lead extension 700 are similar in structure and function to the cables of lead 150. In other words, each cable in lead extension 700 may also be comprised of four concentric layers: a first layer, a second layer, a layer, and an optional fourth layer. The first layer comprises an inner conductor, the second layer comprises an inner insulator, and the third layer comprises an outer conductor. The second layer is configured to electrically isolate the first layer from the third layer. If there is a fourth layer, the fourth layer comprises an outer insulator. However, each cable may comprise other concentric layers, such as other conducting or insulting layers. Additionally, in one embodiment, each cable may have fewer than four concentric layers. The structure and construction of each layer in cables of lead extension 700 is similar to the corresponding layers discussed above in relation to the lead 150. The discussion above regarding the structure of the cables 300 and the structure of cable layers in lead 150 is also applicable here.

Elongated body 704 of lead extension 700 is similar in construction to elongate member 200 of lead 150. Thus, elongated body 704 may include lumens for stylets and other additional layers as discussed above in reference to elongate member 200.

Figure 15:
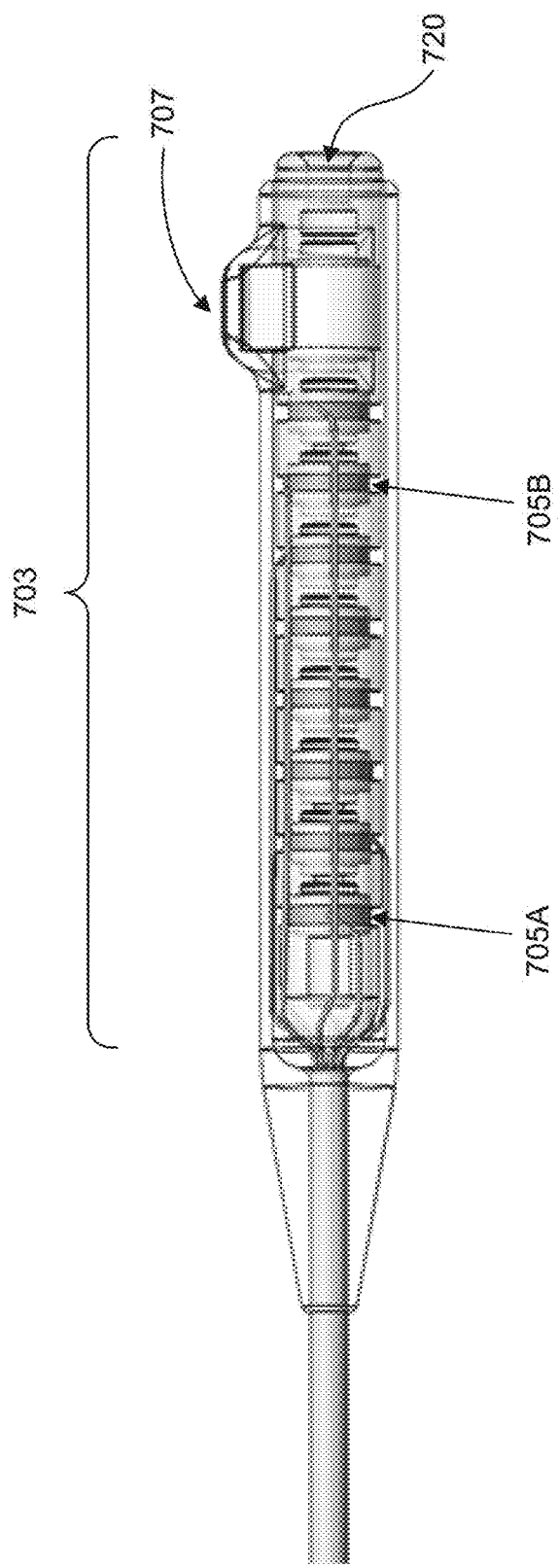
FIG. 15 is a side view of the distal end of the lead extension in FIG. 13 according to one embodiment.
Figure 16:
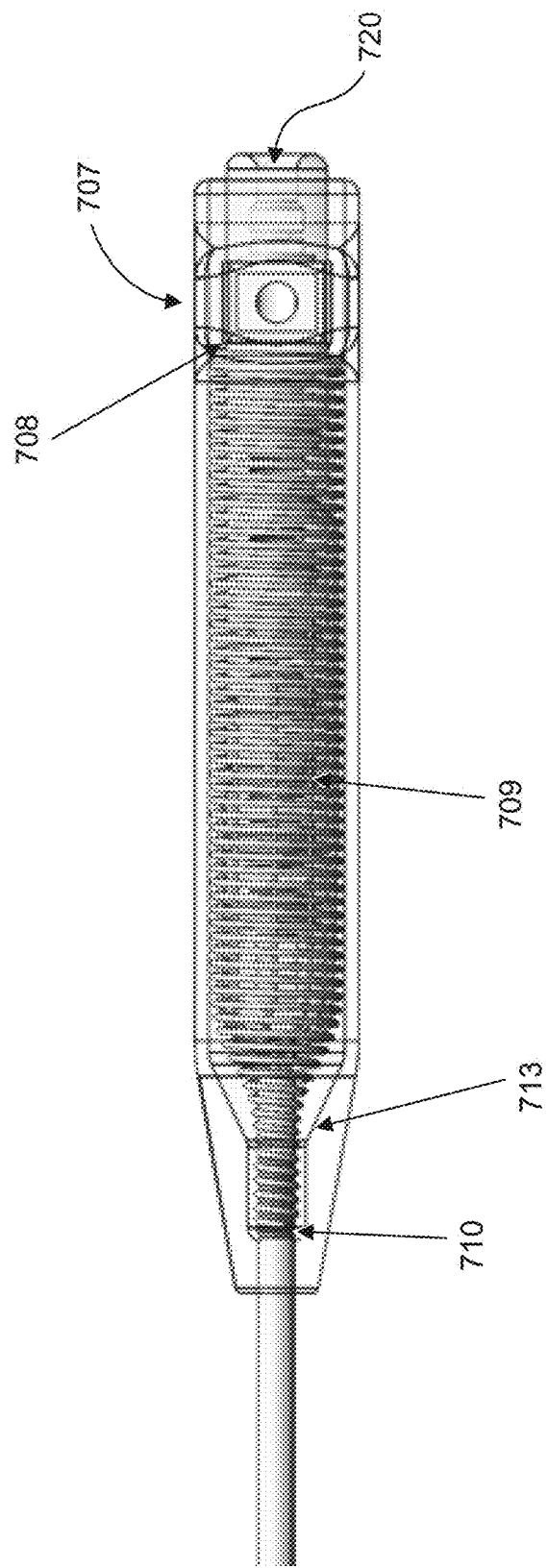
FIG. 16 is another side view of the distal end of lead extension of FIG. 15.
Figure 17:
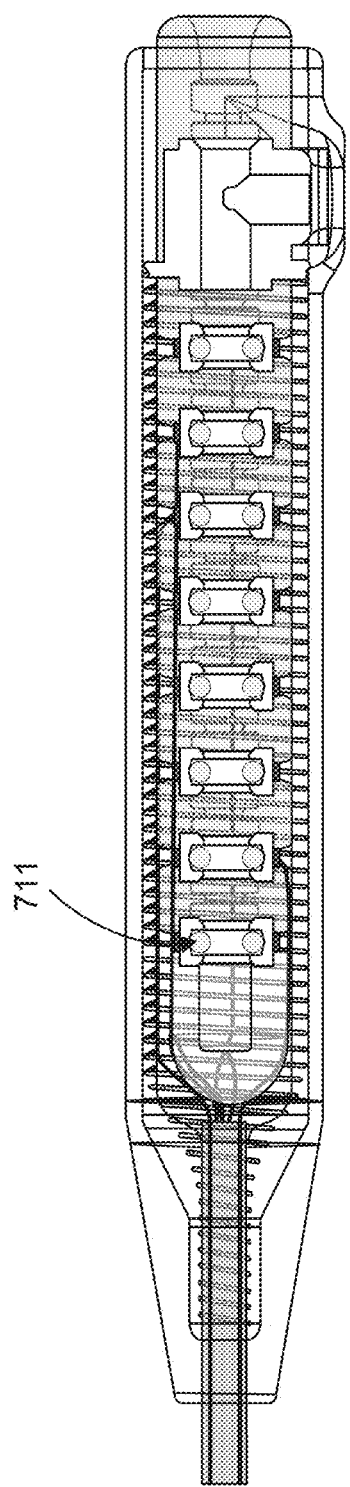
FIG. 17 is a cross-sectional view of the connecting portion of the lead extension of FIG. 15 according to one embodiment.

The distal end 702 of lead extension 700 is different from the distal end 202 of lead 150. The distal end 702 of lead extension is shown in FIGS. 15-17. FIG. 15 has some components of the distal end not illustrated for discussion purposes. The distal end 702 of lead extension 700 has at least one distal electrical contact 705A. In one embodiment, there are eight electrical contacts.

There is a connecting portion 703 disposed at the distal end 702 of lead extension 700. This connecting portion 703 comprises a cavity 720, as shown in FIG. 15. The opening of the cavity 720 is located at the distal end of the lead. The cavity extends throughout the length of the connecting portion 703. The proximal end of lead 150 may be inserted into cavity 720. The connecting portion 703 comprises a fastener 707 that retains the proximal end of the lead 150 in the cavity. In one embodiment, this fastener 707 is a setscrew block. However, other similar functioning fasteners may also be used. The fastener makes contact with the connecting member 240 of the lead 150.

At least one distal electrical contact 705A of the lead extension 700 is electrically connected to at least one electrical contact 220 located on the proximal end 201 of the lead 150. For example, distal electrical contact 705A of lead extension 700 may electrically connect to electrical contact 220A of lead 150 (shown in FIG. 2) and distal electrical contact 705B of lead extension 700 may connect to electrical contact 220H of lead 150 when the proximal end 201 of lead 150 is inserted into the cavity 720. Electrical conductors present in the cavity 720 allow the contacts of the lead to electrically connect with the contacts of the lead extension. In one embodiment, this electrical conductor may be a circumferential garter spring 711, shown in FIG. 17.

Additionally, the connecting portion 703 of the distal end 702 of lead extension 700 further includes a layer of conductive material 709 and a sleeve 713. In one embodiment, the layer of conductive material is a coil wire, as shown in FIG. 16. In other non-limiting embodiments, it may be braided wire. The layer of conductive material 709 is disposed over and concentric with the cavity 720. The sleeve 713 is disposed over and concentric with the layer of conductive material 709. Sleeve 713 is similar in construction to connecting member 240. Thus, the discussion above relating to the material and shape of the connecting member 240 is also applicable to sleeve 713.

At the distal end of lead extension member, the layer of conductive material 709 is welded to the fastener 707 at point 708, as shown in FIG. 16. At a more proximal end, the layer of conductive material 709 is welded at 710 to the sleeve 713.

As discussed above in relation to the lead, in some embodiments of the lead the outer conductor of cables 300 in the lead is grounded through connecting member 240. The structure of the distal end 702 of the lead extension 700, particularly the connecting portion 703, retains this grounding arrangement.

The fastener 707 electrically connects to the electrically active connecting member 240 of the proximal end 201 of lead 150. The fastener 707, in turn, is electrically connected to the conductive coiled wire 709. The coil 709 is electrically connected to the sleeve 713. Sleeve 713, in turn, is connected to the outer conducting layers in the cables of the lead extension.

Additionally, the implantable pulse generator 100 of the system may also include a shielding material. An embodiment of this is shown in FIG. 11.

Figure 11B:
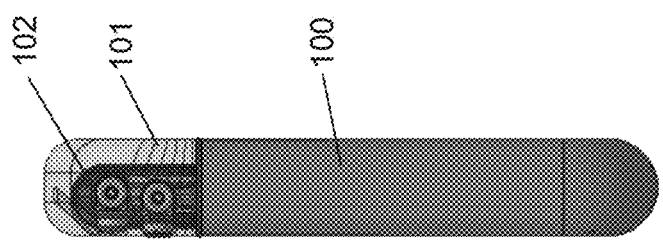
FIG. 11B is a side view of an implantable pulse generator with shielding materials in the header according to one embodiment.
Figure 11A:
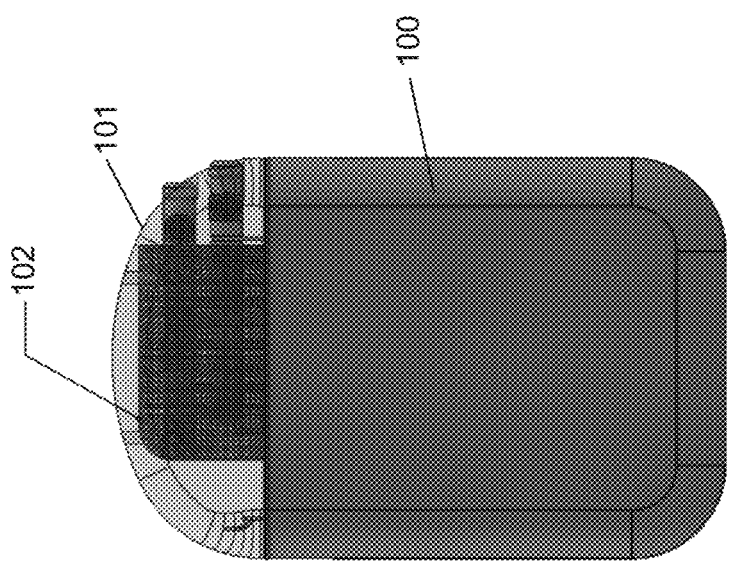
FIG. 11A is a front view of an implantable pulse generator with shielding materials in the header according to one embodiment.

Here, implantable pulse generator 100 has a header 101. The header 101, or a portion of the header, may be comprised of a shielding material. In an embodiment, as seen in FIGS. 11A and 11B, the shielding material 102 may be a cover that is incorporated into the body of the header 101. Alternatively, the shielding material may be disposed over the header. Materials used for this shielding are similar to materials disclosed herein as being appropriate for shielding. For example, the material may be a conductive mesh, as seen in FIG. 11A. Because the proximal end 201 of lead 150 or the proximal end 701 of lead extension 700 is inserted into this header 101, this arrangement shields the proximal end 201 of lead 150 or the proximal end 701 of lead extension 700 when either one is inserted into the header. The length of the proximal end 701 or 201 that is inserted into the header 101 runs from the beginning of proximal end until the location of the connecting member 240 (on lead) or 1440 (on lead extension). This header 101 improves shielding of the lead 150 and enhances the ease of lead manufacturing.

Often times, it may be difficult to manufacture lead 150 with cables that have shields that extend to location of the electrical contacts. When header 101 comprises a shielding material, the shield (inner insulator and outer conductor) may terminate at a location more distal to the electrical contacts, such as for example, at the connecting member 240.

While these embodiments have been described in reference to a lead 150, one of ordinary skill in the art, with the benefit of this disclosure, would be able to apply these concepts to other medical devices, such as catheters and the like. For example, a catheter capable of conducting an electrical signal may comprise cables constructed in the same manner as described above.

Additional Embodiments

In one embodiment, the medical device further comprises an extension member connected to the proximal end of the elongate member. The extension member comprises an elongated body, a distal end, a proximal end, and a connecting portion disposed at the distal end of the elongated body, wherein the proximal end of the elongate member is inserted into the connecting portion of the extension member.

In one embodiment, the medical device comprises eight electrical contacts disposed at the proximal end of the elongate member, eight electrodes disposed at the distal end of the elongate member, and eight cables extending along the elongate member. Each cable electrically connects one electrical contact to one electrode and is individually comprised of three concentric layers. The three layers include a first layer comprising an inner conductor, a second layer comprising an inner insulator, and a third layer comprising an outer conductor. The second layer is configured to electrically isolate the first layer from the third layer.

In one embodiment, a medical device extension for conducting an electrical signal is provided. The medical device extension comprises: an elongated body having a proximal end and a distal end, a proximal electrical contact disposed at the proximal end of the elongated body, a distal electrical contact disposed at the distal end of the elongated body, and a cable extending along the elongated body. The cable electrically connects the proximal electrical contact to the distal electrical contact. The cable comprises three concentric layers which include a first layer comprising an inner conductor, a second layer comprising an inner insulator, and a third layer comprising an outer conductor. The second layer is configured to electrically isolate the first layer from the third layer. In some embodiments, the outer conductor of the cable is configured to reduce electromagnetic interference of an external source of electromagnetic energy on the inner conductor. In some embodiments, the cable of the medical device extension comprises an additional fourth layer, comprising an outer insulator.

In one embodiment, the medical device extension comprises eight electrical contacts disposed at the proximal end of the elongated body, eight electrodes disposed at the distal end of the elongated body, and eight cables extending along the elongated body. Each cable electrically connects one electrical contact to one electrode and is individually comprised of three concentric layers. The three layers include a first layer comprising an inner conductor, a second layer comprising an inner insulator, and a third layer comprising an outer conductor. The second layer is configured to electrically isolate the first layer from the third layer.

In one embodiment, the medical device extension further comprises a connecting portion disposed at the distal end of the elongated body. The connection portion comprises a cavity, a fastener, a layer of conductive material, and a sleeve disposed over the layer of conductive material. The layer of conductive material is electrically connected to the fastener and to the sleeve.

In one embodiment, a medical device for conducting electrical signals has an elongate member with a proximal end and a distal end. A plurality of cables extend along a portion of the elongate member. Each cable comprises three concentric layers: a first layer with an inner conductor, a second layer with an inner insulator, and third layer with an outer conductor. The second layer is configured to substantially electrically isolate the first layer from the third layer.

In one embodiment, the outer conductor of each cable is configured to reduce the electromagnetic interference of an external source of electromagnetic energy on the inner conductor of each cable.

In one embodiment, the inner insulator of at least one cable comprises a wall having a wall thickness of 0.0001 inches to 0.025 inches.

In one embodiment, the inner insulator of each cable extends along a portion of the length of each cable.

In one embodiment, the inner conductor of each cable comprises individual wire filars. In one embodiment, the inner conductor of at least one cable comprises one or more individual wire filars. In one embodiment, the inner conductor of at least one cable comprises less than seven individual wire filars. In one embodiment, at least one individual wire filar has a wire diameter between 0.0001 inches to 0.015 inches. In one embodiment, each individual wire filar of each inner conductor has a wire diameter between 0.0005 inches to 0.0015 inches In one embodiment, the outer conductor of each cable comprises individual wire filars. In one embodiment, the outer conductor of at least one cable comprises one or more individual wire filars. In one embodiment, the outer conductor of at least one cable comprises less than twelve individual wire filars. In one embodiment, at least one individual wire filar of an outer conductor has a diameter between 0.0003 inches to 0.013 inches. In one embodiment, at least one individual wire filar has a rectangular cross section.

In one embodiment, the diameter of at least one inner conductor filar is different than the diameter of at least one outer conductor filar.

In one embodiment, the medical device further includes at least one electrical contact at the proximal end of the elongate member. This electrical contact is electrically coupled to the inner conductor of at least one cable. In one embodiment, the medical device has at least eight electrical contacts and at least eight cables. Each electrical contact is electrically coupled to the inner conductor of the eight cables.

In one embodiment, the medical device further includes at least one electrode at the distal end of the elongate member. The electrode is electrically coupled to the inner conductor of at least one cable. In one embodiment, the medical device has at least eight electrodes and at least eight cables. Each electrode is electrically coupled to the inner conductor of the eight cables.

In one embodiment, a medical device for carrying electric signal has an elongate member with a proximal end and a distal end. A plurality of cables extend along a portion of the elongate member. Each cable comprises four concentric layers: a first layer with an inner conductor, a second layer with an inner insulator, third layer with an outer conductor, and a fourth layer comprised of an outer insulator. The second layer is configured to substantially electrically isolate the first layer from the second layer. The fourth layer is configured to substantially electrically isolate the third layer from its surroundings.

In one embodiment, the fourth layer comprises static dissipative material. In one embodiment, the fourth layer comprises heat shrink tubing. In one embodiment, the fourth layer extends along a portion of the cable.

In one embodiment, the outer insulator of at least one cable comprises a wall with a wall thickness of 0.0005 inches to 0.0015 inches. In one embodiment, the inner insulator of at least one cable has the same or greater wall thickness than the outer insulator of at least one cable.

In one embodiment, the medical device includes a pulse generator with a grounding material. The connecting member is electrically coupled to the grounding material of the pulse generator.

In one embodiment, the pulse generator is electrically coupled to the inner conductor of at least one cable and electrically isolated from the outer conductor of at least one cable.

In one embodiment, the medical device includes a connecting member near the proximal end of the elongate member. In one embodiment, the connecting member is electrically inactive.

In one embodiment, the connecting member is electrically active and coupled to the outer conductor of at least one cable.

In one embodiment, the plurality of cables extend in parallel to each other along the elongate member. In one embodiment, there are a plurality of channels in the elongate member and the plurality of cables are located in the plurality of channels.

In one embodiment, a lumen extends along a portion of the elongate member.

In one embodiment, the outer conductor comprises an outer layer and an inner core. In one embodiment, the inner core is selected from a group consisting of silver, copper, gold, palladium, tantalum, platinum, and nickel. In one embodiment, the outer layer is selected from a group consisting of MP35N alloy, tantalum, palladium, stainless steel, platinum, and nitinol.

In one embodiment, the outer conductor is a Drawn Filled Tube.

In one embodiment, the outer conductor has a coil construction. In one embodiment, the outer conductor has a braided construction. In one embodiment, the outer conductor is comprised of a laser cut tube. In one embodiment, the laser cut tube has a cut extending along its length.

In one embodiment, the device further comprises a shielding layer radially encompassing the elongate member. In one embodiment, the shielding layer comprises of a conductive tape. In one embodiment, the conductive tape comprises a conductive material disposed on a polymer.

In one embodiment, the medical device further comprises a pulse generator comprising a header portion. In one embodiment, the header portion comprises a shielding material. In one embodiment, the shielding material is a mesh.

In one embodiment, the elongate member of the medical device and the outer insulator comprise microscopic holes.

In one embodiment, the device further comprises an insulating layer radially encompassing the elongate member.

Additional embodiments include methods of manufacturing MRI compatible medical devices by configuring a medical device to include one or more insulator combinations as described above.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Further, references herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. The breadth and scope of the invention should not be limited by any of the above-described exemplary embodiments, but should be defined only in accordance with the following claims and their equivalents.

What is claimed is:

1. A medical device for conducting an electrical signal comprising:
    an elongate member with a proximal end and a distal end;
    a plurality of electrical contacts disposed at the proximal end of the elongate member; and
    a plurality of cables extending along a portion of the elongate member, each cable electrically coupled to only one of the plurality of electrical contacts,
    wherein each cable comprises three concentric layers including:
        a first layer comprising an inner conductor,
        a second layer comprising an inner insulator, and
        a third layer comprising an outer conductor, wherein the second layer is configured to substantially electrically isolate the first layer from the third layer.

2. The device of claim 1, wherein the outer conductor of each cable is configured to reduce electromagnetic interference of an external source of electromagnetic energy on the inner conductor of each cable.

3. The device of claim 1, wherein the inner insulator of at least one cable comprises a wall having a wall thickness of 0.0001 inches to 0.025 inches.

4. The device of claim 1, wherein the inner insulator of each cable extends along a portion of the length of each cable.

5. The device of claim 1, wherein the inner conductor of each cable comprises individual wire filars.

6. The device of claim 5, wherein at least one individual wire filar has a wire diameter between 0.0001 inches to 0.015 inches.

7. The device of claim 5, wherein each individual wire filar of each inner conductor has a wire diameter between 0.0005 inches to 0.0015 inches.

8. The device of claim 1, wherein the inner conductor of at least one cable comprises one or more individual wire filars.

9. The device of claim 5, wherein the inner conductor of at least one cable comprises less than 7 individual wire filars.

10. The device of claim 1, wherein the outer conductor of each cable comprises individual wire filars.

11. The device of claim 10, wherein the outer conductor of at least one cable comprises one or more individual wire filars.

12. The device of claim 10, wherein the outer conductor of at least one cable comprises less than 12 individual wire filars.

13. The device of claim 10, wherein at least one individual wire filar has a diameter between 0.0003 inches to 0.013 inches.

14. The device of claim 10,
wherein the inner conductor of each cable comprises individual wire filars; and
wherein the diameter of at least one inner conductor filar is different than the diameter of at least one outer conductor filar.

15. The device of claim 1, wherein each cable further comprises a fourth concentric layer comprised of an outer insulator; wherein the fourth layer is configured to substantially electrically isolate the third layer from its surroundings.

16. The device of claim 15, wherein the outer insulator of at least one cable has a wall with a wall thickness of 0.0005 inches to 0.0015 inches.

17. The device of claim 15, wherein the inner insulator of at least one cable has the same or greater wall thickness than the outer insulator of at least one cable.

18. The device of claim 1, wherein each electrical contact is electrically coupled to the inner conductor of at least one cable.

19. The device of claim 18, comprising at least 8 electrical contacts at the proximal end of the elongate member and at least 8 cables, wherein the 8 electrical contacts are electrically coupled to the inner conductors of the 8 cables.

20. The device of claim 1, further comprising at least one electrode at the distal end of the elongate member, wherein the at least one electrode is electrically coupled to the inner conductor of at least one cable.

21. The device of claim 20, comprising at least 8 electrodes at the distal end of the elongate member and at least 8 cables, wherein the at least 8 electrodes are electrically coupled to the inner conductors of the at least 8 cables.

22. The device of claim 1, further comprising a connecting member near the proximal end of the elongate member.

23. The device of claim 22, wherein the connecting member is electrically inactive.

24. The device of claim 22, further comprising a pulse generator with a grounding material, wherein the connecting member is electrically coupled to the grounding material of the pulse generator.

25. The device of claim 24, wherein the outer conductor of at least one cable is electrically coupled to the connecting member.

26. The device of claim 1, further comprising a pulse generator, wherein the pulse generator is electrically coupled to the inner conductor of at least one cable and electrically isolated from the outer conductor of at least one cable.

27. The device of claim 1, wherein the plurality of cables extend in parallel to each other along the elongate member.

28. The device of claim 1, further comprising:
a plurality of channels in the elongate member;
wherein the plurality of cables are located within the plurality of channels.

29. The device of claim 1, further comprising a lumen extending along a portion of the elongate member.

30. The device of claim 1, wherein the outer conductor comprises an outer layer and an inner core.

31. The device of claim 30, wherein the inner core is selected from a group consisting of: silver, copper, gold, palladium, tantalum, platinum, and nickel.

32. The device of claim 30, wherein the outer layer is selected from a group consisting of: MP35N alloy, tantalum, palladium, stainless steel, platinum, and nitinol.

33. The device of claim 1, wherein the outer conductor has a coil construction.

34. The device of claim 1, wherein the outer conductor has a braided construction.

35. The device of claim 1, wherein the outer conductor is comprised of a laser cut tube.

36. The device of claim 35, wherein the laser cut tube has a cut extending among its length.

37. The device of claim 10, wherein at least one individual wire filar has a rectangular cross section.

38. The device of claim 15, wherein the fourth layer comprises static dissipative material.

39. The device of claim 15, wherein the fourth layer comprises heat shrink tubing.

40. The device of claim 15, wherein the fourth layer extends along a portion of the cable.

41. The device of claim 1, further comprising a shielding layer radially encompassing the elongate member.

42. The device of claim 1, further comprising an insulating layer radially encompassing the elongate member.

43. The device of claim 1, further comprising a pulse generator comprising a header portion, wherein the header portion comprises a shielding material.

44. The device of claim 43, wherein the shielding material is a mesh.

45. The device of claim 41, wherein the shielding layer is comprised of a conductive tape.

46. The device of claim 45, wherein the conductive tape comprises a conductive material disposed on a polymer.

47. The device of claim 15, wherein the elongate body and the fourth layer comprise microscopic holes.

48. A medical device for conducting an electrical signal comprising:
an elongate member with a proximal end and a distal end; and
a plurality of cables extending along a portion of the elongate member,
wherein each cable comprises three concentric layers including:
a first layer comprising an inner conductor,
a second layer comprising an inner insulator, and
a third layer comprising an outer conductor, wherein the second layer is configured to substantially electrically isolate the first layer from the third layer, and wherein the outer conductor of each cable is configured to reduce electromagnetic interference of an external source of electromagnetic energy on the inner conductor of each cable.

49. A medical device for conducting an electrical signal comprising:
- an elongate member with a proximal end and a distal end;
- a plurality of electrodes disposed at the distal end of the elongate member; and
- a plurality of cables extending along a portion of the elongate member, each cable electrically coupled to only one of the plurality of electrodes,
- wherein each cable comprises three concentric layers including:
  - a first layer comprising an inner conductor,
  - a second layer comprising an inner insulator, and
  - a third layer comprising an outer conductor, wherein the second layer is configured to substantially electrically isolate the first layer from the third layer.

50. The device of claim 49, wherein the outer conductor of each cable is configured to reduce electromagnetic interference of an external source of electromagnetic energy on the inner conductor of each cable.

51. The device of claim 49, wherein the inner insulator of each cable extends along a portion of the length of each cable.

52. The device of claim 49, wherein the inner conductor of at least one cable comprises one or more individual wire filars.

53. The device of claim 49, wherein the inner conductor of each cable comprises individual wire filars.

54. The device of claim 49, wherein the outer conductor of each cable comprises individual wire filars.

55. The device of claim 49, wherein each cable further comprises a fourth concentric layer comprised of an outer insulator; wherein the fourth layer is configured to substantially electrically isolate the third layer from its surroundings.

56. The device of claim 49, further comprising at least one electrical contact at the proximal end of the elongate member, wherein the electrical contact is electrically coupled to the inner conductor of at least one cable.

* * * * *